(12) United States Patent
Dhanoa

(10) Patent No.: US 8,927,553 B2
(45) Date of Patent: Jan. 6, 2015

(54) DEUTERIUM-ENRICHED ALKYL SULFONAMIDES AND USES THEREOF

(71) Applicant: Daljit Singh Dhanoa, Del Mar, CA (US)

(72) Inventor: Daljit Singh Dhanoa, Del Mar, CA (US)

(*) Notice: Subject to any disclaimer, the term of this patent is extended or adjusted under 35 U.S.C. 154(b) by 0 days.

(21) Appl. No.: 13/954,803

(22) Filed: Jul. 30, 2013

(65) Prior Publication Data

US 2014/0221395 A1    Aug. 7, 2014

Related U.S. Application Data

(63) Continuation-in-part of application No. 12/806,279, filed on Aug. 9, 2010, now Pat. No. 8,530,479.

(60) Provisional application No. 61/273,767, filed on Aug. 10, 2009.

(51) Int. Cl.
| | |
|---|---|
| *A61K 31/495* | (2006.01) |
| *A61K 45/06* | (2006.01) |
| *C07D 295/155* | (2006.01) |
| *C07D 295/135* | (2006.01) |

(52) U.S. Cl.
CPC .......... *C07D 295/155* (2013.01); *A61K 31/495* (2013.01); *A61K 45/06* (2013.01); *C07D 295/135* (2013.01)
USPC ...................... 514/255.03; 544/393

(58) Field of Classification Search
USPC ...................... 514/255.03; 544/393
See application file for complete search history.

(56) References Cited

U.S. PATENT DOCUMENTS 7,153,858 B2 * 12/2006 Dhanoa et al. ........... 514/253.01

* cited by examiner

*Primary Examiner* — Kristin Vajda
(74) *Attorney, Agent, or Firm* — Karl Neidert

(57) ABSTRACT

The present invention is concerned with deuterium-enriched sulfonamides of formula 1, their pharmaceutically acceptable salts and methods of use thereof for the treatment of anxiety disorders including, General Anxiety Disorder (GAD), Panic Disorder (PD), Post-Traumatic Stress Disorder (PTSD), Social Phobia (SP), Health Anxiety (Hypochondriasis), depression, major depressive disorders, unipolar depression, bipolar I depression disorder, bipolar II depression disorder, treatment-resistant depression, single episodic and recurrent major depressive disorders, depression in the medically ill, attention deficit hyperactivity disorder (ADHD), attention deficit disorder (ADD), Obsessive-Compulsive Disorder (OCD), Obsessive-Compulsive Personality Disorder (OCPD), Autism Spectrum Disorder (ASD), schizophrenia, psychosis, epilepsy, seizures, hot flashes due to menopause, age-related macular degeneration (AMD), premature ejaculation, male erectile dysfunction, sexual dysfunction, obesity, eating disorders, bulimia nervosa, anorexia nervosa, angina, migraine, pain, nociception, sleep disorders, insomnia, fibromyalgia, alcohol withdrawal, autism, Rett's syndrome, cyclothymic disorder, neural injury, neurodegenerative diseases, Parkinson's disease, Parkinson's disease psychosis, Huntington disease, Alzheimer's disease, frontotemporal dementia, cognitive impairment associated with age-related dementia, Alzheimer's disease, schizophrenia, psychosis, depression, pain or discomfort associated with surgery and pain or discomfort associated with medical illness.

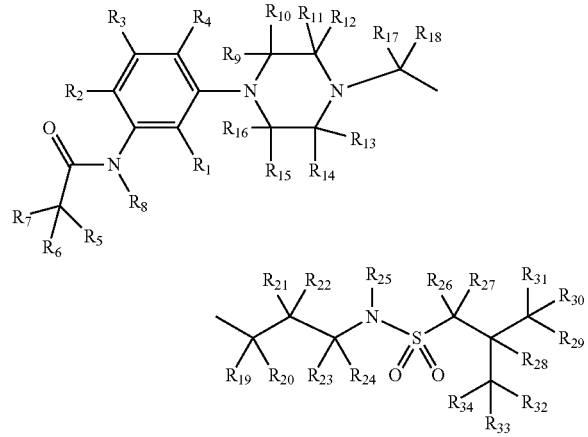

20 Claims, No Drawings

DEUTERIUM-ENRICHED ALKYL SULFONAMIDES AND USES THEREOF

CROSS-REFERENCE TO RELATED APPLICATIONS

This application is a continuation-in-part (CIP) of U.S. patent application Ser. No. 12/806,279, filed on Aug. 9, 2010, which is incorporated herein by reference in its entirety. U.S. patent application Ser. No. 12/806,279 claims the benefit of priority to U.S. Provisional Application No. 61/273,767, filed on Aug. 10, 2009.

FIELD OF THE INVENTION

The present invention generally relates to deuterium-enriched N-acetylamino-(piperazinyl)-butyl)-alkylsulfonamides of formula 1, their pharmaceutically acceptable salts, synthesis and methods of use thereof. These compounds are 5-HT (serotonin) receptor modulators more specifically partial agonists, agonists, antagonists or inverse agonists, and Selective Serotonin Reuptake Inhibitors (SSRI) found to be useful as therapeutic agents for the treatment of anxiety disorders including, General Anxiety Disorder (GAD), Panic Disorder (PD), Post-Traumatic Stress Disorder (PTSD), Social Phobia (SP), Health Anxiety (Hypochondriasis), depression, major depressive disorders, unipolar depression, bipolar I depression disorder, bipolar II depression disorder, treatment-resistant depression, single episodic and recurrent major depressive disorders, depression in the medically ill, attention deficit hyperactivity disorder (ADHD), attention deficit disorder (ADD), Obsessive-Compulsive Disorder (OCD), Obsessive-Compulsive Personality Disorder (OCPD), Autism Spectrum Disorder (ASD), schizophrenia, psychosis, epilepsy, seizures, age-related macular degeneration (AMD), premature ejaculation, male erectile dysfunction, sexual dysfunction, obesity, eating disorders, bulimia nervosa, anorexia nervosa, angina, migraine, pain, nociception, sleep disorders, insomnia fibromyalgia, alcohol withdrawal, autism, Rett's syndrome, cyclothymic disorder, neural injury, neurodegenerative diseases, Parkinson's disease, Parkinson's disease psychosis, Huntington disease, Alzheimer's disease, frontotemporal dementia, cognitive impairment associated with age-related dementia, Alzheimer's disease, schizophrenia, psychosis, depression, pain or discomfort associated with surgery and pain or discomfort associated with medical illness.

SUMMARY OF THE INVENTION

The present invention is concerned with deuterium-enriched sulfonamides of formula 1, pharmaceutically acceptable salts and methods of use thereof, wherein:
$R_1$, $R_2$, $R_3$, and $R_4$ are independently selected from D, H or F;

$R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$ and $R_{24}$ are independently selected from D or H;

$R_{25}$ is selected from H, D or $CD_3$;

$R_{26}$, $R_{27}$, $R_{28}$, $R_{29}$, $R_{30}$, $R_{31}$, $R_{32}$, $R_{33}$, $R_{34}$ are independently selected from D and H;

$R_{29}$ and $R_{32}$ are joined together to form cyclic rings including cyclohexyl, cycloheptyl, cyclopentyl, cyclobutyl or cyclopropyl;

for the treatment of anxiety disorders including, General Anxiety Disorder (GAD), Panic Disorder (PD), Post-Traumatic Stress Disorder (PTSD), Social Phobia (SP), Health Anxiety (Hypochondriasis), depression, major depressive disorders, unipolar depression, bipolar I depression disorder, bipolar II depression disorder, treatment-resistant depression, single episodic and recurrent major depressive disorders, depression in the medically ill, attention deficit hyperactivity disorder (ADHD), attention deficit disorder (ADD), Obsessive-Compulsive Disorder (OCD), Obsessive-Compulsive Personality Disorder (OCPD), Autism Spectrum Disorder (ASD), schizophrenia, psychosis, epilepsy, seizures, hot flashes due to menopause, age-related macular degeneration (AMD), premature ejaculation, male erectile dysfunction, sexual dysfunction, obesity, eating disorders, bulimia nervosa, anorexia nervosa, smoking cessation, angina, migraine, pain, nociception, sleep disorders, insomnia fibromyalgia, alcohol withdrawal, autism, Rett's syndrome, cyclothymic disorder, neural injury, neurodegenerative diseases, Parkinson's disease, Parkinson's disease psychosis, Huntington disease, Alzheimer's disease, frontotemporal dementia, cognitive impairment associated with age-related dementia, Alzheimer's disease, schizophrenia, psychosis, depression, pain or discomfort associated with surgery or pain and discomfort associated with medical illness.

The present invention relates to the invention of new compounds for treating a subject afflicted with a condition (disease and/or disorder) requiring a treatment, by administering an effective amount of a compound of the invention to treat the condition(s). Various diseases and/or disorders will be responsive to the introduction of the compounds, alone and/or in combination with other drugs; or the compounds may be utilized to alter physiological phenomena associated with conditions (diseases or disorders) to achieve a desired treatment of said(s) condition(s) alone and/or in combination with other drugs.

The compounds of the invention may also be used for vasodilation, smooth muscle contraction, bronchoconstriction, brain disorders such as vascular disorders, blood flow disorders caused by vasodilation and vasospastic diseases

1 such as vascular headache, migraine and Reynaud's disease. The compounds may also be used for neurodegenerative diseases including Parkinson's, Alzheimer's and Huntington disease. The compounds may also be used for cardiovascular diseases such as stroke and cerebral ischemia. The compounds may also be used for the treatment of intestinal tract related disturbances of the serotoninergic system. The compounds may also be useful in the treatment of stress-related somatic disorders and sympathetic dystrophy such as shoulder and hand syndrome. The compounds may also be useful in the treatment of bladder function disorders such as cystitis, bladder detrusor hyper-reflexia, and bladder and urinary incontinence. The compounds may also be useful in the treatment of nociception or pain associated with or attributable to any of the foregoing conditions.

One advantage of the compounds of the invention is that they were discovered to be both 5-HT modulators e.g. agonists, inverse agonists or antagonists and have SSRI type effects. These compounds are effective in treating, preventing or curing 5-HT related disorders or diseases.

In one aspect, the compounds of the invention are 5-HT modulators (agonists, partial agonists or antagonists) and/or selective serotonin reuptake inhibitors (SSRI). The compounds of the present invention are 5-HT$_{1A}$ receptor modulators specifically 5-HT$_{1A}$ partial agonists as shown by their high binding affinity (Ki) in the range of 1 nM-1000 nM and functional activity (EC$_{50}$) in the range of 1 nM-2000 nM for the 5-HT$_{1A}$ receptor. These compounds also shown to have activity for other 5-HT receptor subtypes as well as dopamine receptors in the range of 10 nM-2500 nM. The compounds of this invention also show activity as selective serotonin reuptake inhibitors in the range of 1 nM-1000 nM.

One object of the present invention is to provide deuterium-enriched compounds of formula 1, or derivative, solvate or a pharmaceutically acceptable salt thereof.

It is another object of the present invention to provide pharmaceutical compositions comprising pharmaceutically acceptable carrier and a therapeutically effective amount of at least one of the deuterium-enriched compounds of the present invention or a pharmaceutically acceptable salt thereof.

Another object of the present invention is a pharmaceutical composition comprising an amount of a compound of formula 1 effective to treat Anxiety in a mammal such as human suffering therefrom, and a pharmaceutically acceptable carrier.

Another object of the present invention is a pharmaceutical composition comprising an amount of a compound of formula 1 effective to treat Panic Disorder (PD) in a mammal such as human suffering therefrom, and a pharmaceutically acceptable carrier.

Another object of the present invention is a pharmaceutical composition comprising an amount of a compound of formula 1 effective to treat Post-Traumatic Stress Disorder (PTSD), in a mammal such as human suffering therefrom, and a pharmaceutically acceptable carrier.

Another object of the present invention is a pharmaceutical composition comprising an amount of a compound of formula 1 effective to treat Social Phobia (SP), in a mammal such as human suffering therefrom, and a pharmaceutically acceptable carrier.

Another object of the present invention is a pharmaceutical composition comprising an amount of a compound of formula 1 effective to treat Health Anxiety (Hypochondriasis), in a mammal such as human suffering therefrom, and a pharmaceutically acceptable carrier.

Another object of the present invention is a pharmaceutical composition comprising an amount of a compound of formula 1 effective to treat Depression, in a mammal such as human suffering therefrom, and a pharmaceutically acceptable carrier.

Another object of the present invention is a pharmaceutical composition comprising an amount of a compound of formula 1 effective to treat Major Depressive Disorder (MDD), in a mammal such as human suffering therefrom, and a pharmaceutically acceptable carrier.

Another object of the present invention is a pharmaceutical composition comprising an amount of a compound of formula 1 in combination with opioid antagonist such as Naltrexone hydrochloride salt, or Samidorphan or opioid partial agonist/antagonist buprenorphine or a balanced combination

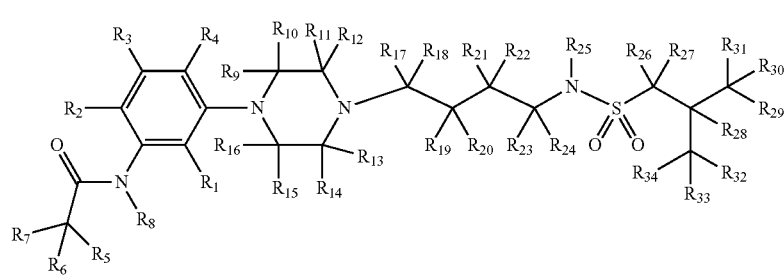

1

It is another object of the present invention to provide pharmaceutical compositions comprising pharmaceutically acceptable carrier and a therapeutically effective amount of at least one of the deuterium-enriched compounds of the present invention or a pharmaceutically acceptable salt thereof, as a single medicine or in combination with other therapeutic agents.

Another object of the present invention is a pharmaceutical composition comprising an amount of a compound of formula 1 effective to treat anxiety disorders including General Anxiety Disorder (GAD) in a mammal such as human suffering therefrom, and a pharmaceutically acceptable carrier.

of all effective to treat Major Depressive Disorder (MDD), in a mammal such as human suffering therefrom, and a pharmaceutically acceptable carrier.

Another object of the present invention is a pharmaceutical composition comprising an amount of a compound of formula 1 effective to treat Unipolar Depression, in a mammal such as human suffering therefrom, and a pharmaceutically acceptable carrier.

Another object of the present invention is a pharmaceutical composition comprising an amount of a compound of formula 1 effective to treat Bipolar I Depression Disorder, in a mammal such as human suffering therefrom, and a pharmaceutically acceptable carrier.

Another object of the present invention is a pharmaceutical composition comprising an amount of a compound of formula 1 effective to treat Bipolar II Depression Disorder, in a mammal such as human suffering therefrom, and a pharmaceutically acceptable carrier.

Another object of the present invention is a pharmaceutical composition comprising an amount of a compound of formula 1 effective to treat Treatment-resistant Depression Disorder, in a mammal such as human suffering therefrom, and a pharmaceutically acceptable carrier.

Another object of the present invention is a pharmaceutical composition comprising an amount of a compound of formula 1 effective to treat Single Episodic and Recurrent Major Depressive Disorders, in a mammal such as human suffering therefrom, and a pharmaceutically acceptable carrier.

Another object of the present invention is a pharmaceutical composition comprising an amount of a compound of formula 1 effective to treat Depression in the medically ill, in a mammal such as human suffering therefrom, and a pharmaceutically acceptable carrier.

Another object of the present invention is a pharmaceutical composition comprising an amount of a compound of formula 1 effective to treat Attention Deficit Hyperactivity Disorder (ADHD), in a mammal such as human suffering therefrom, and a pharmaceutically acceptable carrier.

Another object of the present invention is a pharmaceutical composition comprising an amount of a compound of formula 1 effective to treat Attention Deficit Disorder (ADD), in a mammal such as human suffering therefrom, and a pharmaceutically acceptable carrier.

Another object of the present invention is a pharmaceutical composition comprising an amount of a compound of formula 1 effective to treat Obsessive-Compulsive Disorder (OCD), in a mammal such as human suffering therefrom, and a pharmaceutically acceptable carrier.

Another object of the present invention is a pharmaceutical composition comprising an amount of a compound of formula 1 effective to treat Obsessive-Compulsive Personality Disorder (OCPD), in a mammal such as human suffering therefrom, and a pharmaceutically acceptable carrier.

Another object of the present invention is a pharmaceutical composition comprising an amount of a compound of formula 1 effective to treat Autism Spectrum Disorder (ASD), in a mammal such as human suffering therefrom, and a pharmaceutically acceptable carrier.

Another object of the present invention is a pharmaceutical composition comprising an amount of a compound of formula 1 effective to treat Schizophrenia, in a mammal such as human suffering therefrom, and a pharmaceutically acceptable carrier.

Another object of the present invention is a pharmaceutical composition comprising an amount of a compound of formula 1 effective to treat psychosis, in a mammal such as human suffering therefrom, and a pharmaceutically acceptable carrier.

Another object of the present invention is a pharmaceutical composition comprising an amount of a compound of formula 1 effective to treat epilepsy, in a mammal such as human suffering therefrom, and a pharmaceutically acceptable carrier.

Another object of the present invention is a pharmaceutical composition comprising an amount of a compound of formula 1 effective to treat seizures, in a mammal such as human suffering therefrom, and a pharmaceutically acceptable carrier.

Another object of the present invention is a pharmaceutical composition comprising an amount of a compound of formula 1 effective to treat hot flashes due to menopause, in a mammal such as human suffering therefrom, and a pharmaceutically acceptable carrier Another object of the present invention is a pharmaceutical composition comprising an amount of a compound of formula 1 effective to treat Age-related Macular Degeneration (AMD), in a mammal such as human suffering therefrom, and a pharmaceutically acceptable carrier.

Another object of the present invention is a pharmaceutical composition comprising an amount of a compound of formula 1 effective to treat Premature Ejaculation, in a mammal such as human suffering therefrom, and a pharmaceutically acceptable carrier.

Another object of the present invention is a pharmaceutical composition comprising an amount of a compound of formula 1 effective to treat Male Erectile Dysfunction, in a mammal such as human suffering therefrom, and a pharmaceutically acceptable carrier.

Another object of the present invention is a pharmaceutical composition comprising an amount of a compound of formula 1 effective to treat Sexual Dysfunction, in a mammal such as human suffering therefrom, and a pharmaceutically acceptable carrier.

Another object of the present invention is a pharmaceutical composition comprising an amount of a compound of formula 1 effective to treat Obesity, in a mammal such as human suffering therefrom, and a pharmaceutically acceptable carrier.

Another object of the present invention is a pharmaceutical composition comprising an amount of a compound of formula 1 effective to treat Eating Disorders such as bulimia nervosa and anorexia nervosa, in a mammal such as human suffering therefrom, and a pharmaceutically acceptable carrier.

Another object of the present invention is a pharmaceutical composition comprising an amount of a compound of formula 1 effective to treat Angina, in a mammal such as human suffering therefrom, and a pharmaceutically acceptable carrier.

Another object of the present invention is a pharmaceutical composition comprising an amount of a compound of formula 1 effective to treat Migraine, in a mammal such as human suffering therefrom, and a pharmaceutically acceptable carrier.

Another object of the present invention is a pharmaceutical composition comprising an amount of a compound of formula 1 effective to treat Pain, in a mammal such as human suffering therefrom, and a pharmaceutically acceptable carrier.

Another object of the present invention is a pharmaceutical composition comprising an amount of a compound of formula 1 effective to treat Nociception, in a mammal such as human suffering therefrom, and a pharmaceutically acceptable carrier.

Another object of the present invention is a pharmaceutical composition comprising an amount of a compound of formula 1 effective to treat Sleep Disorders, in a mammal such as human suffering therefrom, and a pharmaceutically acceptable carrier.

Another object of the present invention is a pharmaceutical composition comprising an amount of a compound of formula 1 effective to treat Insomnia, in a mammal such as human suffering therefrom, and a pharmaceutically acceptable carrier.

Another object of the present invention is a pharmaceutical composition comprising an amount of a compound of formula 1 effective to treat Alcohol Withdrawal, in a mammal such as human suffering therefrom, and a pharmaceutically acceptable carrier.

Another object of the present invention is a pharmaceutical composition comprising an amount of a compound of formula 1 effective to treat Fibromyalgia, in a mammal such as human suffering therefrom, and a pharmaceutically acceptable carrier.

Another object of the present invention is a pharmaceutical composition comprising an amount of a compound of formula 1 effective to treat Autism, in a mammal such as human suffering therefrom, and a pharmaceutically acceptable carrier.

Another object of the present invention is a pharmaceutical composition comprising an amount of a compound of formula 1 effective to treat Rett's Syndrome, in a mammal such as human suffering therefrom, and a pharmaceutically acceptable carrier.

Another object of the present invention is a pharmaceutical composition comprising an amount of a compound of formula 1 effective to treat Cyclothymic Disorder, in a mammal such as human suffering therefrom, and a pharmaceutically acceptable carrier.

Another object of the present invention is a pharmaceutical composition comprising an amount of a compound of formula 1 effective to treat Neural Injury, in a mammal such as human suffering therefrom, and a pharmaceutically acceptable carrier.

Another object of the present invention is a pharmaceutical composition comprising an amount of a compound of formula 1 effective to treat Neurodegenerative Diseases, in a mammal such as human suffering therefrom, and a pharmaceutically acceptable carrier.

Another object of the present invention is a pharmaceutical composition comprising an amount of a compound of formula 1 effective to treat Parkinson's Disease, in a mammal such as human suffering therefrom, and a pharmaceutically acceptable carrier.

Another object of the invention is a method of treating Parkinson's disease or Parkinson's disease psychosis comprising administering a pharmaceutically effective amount of a compound of formula 1 with one or more drugs selected from the group consisting of pimavanserin, levodopa, carbidopa, pramipexol, ropinirole and bromocriptine.

Another object of the present invention is a pharmaceutical composition comprising an amount of a compound of formula 1 effective to treat Parkinson's Disease Psychosis, in a mammal such as human suffering therefrom, and a pharmaceutically acceptable carrier.

Another object of the present invention is a pharmaceutical composition comprising an amount of a compound of formula 1 effective to treat Huntington Disease, in a mammal such as human suffering therefrom, and a pharmaceutically acceptable carrier.

Another object of the present invention is a pharmaceutical composition comprising an amount of a compound of formula 1 effective to treat Alzheimer's Disease, in a mammal such as human suffering therefrom, and a pharmaceutically acceptable carrier.

Another object of the present invention is a pharmaceutical composition comprising an amount of a compound of formula 1 effective to treat Frontotemporal Dementia, in a mammal such as human suffering therefrom, and a pharmaceutically acceptable carrier.

Another object of the present invention is a pharmaceutical composition comprising an amount of a compound of formula 1 effective to treat Cognitive Impairment associated with Age-related Dementia, in a mammal such as human suffering therefrom, and a pharmaceutically acceptable carrier.

Another object of the present invention is a pharmaceutical composition comprising an amount of a compound of formula 1 effective to treat Cognitive Impairment associated with Alzheimer's Disease, in a mammal such as human suffering therefrom, and a pharmaceutically acceptable carrier.

Another object of the present invention is a pharmaceutical composition comprising an amount of a compound of formula 1 effective to treat Cognitive Impairment associated with Schizophrenia, in a mammal such as human suffering therefrom, and a pharmaceutically acceptable carrier.

Another object of the present invention is a pharmaceutical composition comprising an amount of a compound of formula 1 effective to treat Cognitive Impairment associated with Psychosis, in a mammal such as human suffering therefrom, and a pharmaceutically acceptable carrier.

Another object of the present invention is a pharmaceutical composition comprising an amount of a compound of formula 1 effective to treat Cognitive Impairment associated with Depression, in a mammal such as human suffering therefrom, and a pharmaceutically acceptable carrier.

Another object of the present invention is a pharmaceutical composition comprising an amount of a compound of formula 1 effective to treat Cognitive Impairment associated with Surgery, in a mammal such as human suffering therefrom, and a pharmaceutically acceptable carrier.

Another object of the present invention is a pharmaceutical composition comprising an amount of a compound of formula 1 effective to treat Cognitive Impairment associated with any medical illness, in a mammal such as human suffering therefrom, and a pharmaceutically acceptable carrier.

Another object of the present invention is a pharmaceutical composition comprising an amount of a compound of formula 1 effective to treat age-related macular degeneration (AMD) in a mammal such as human suffering therefrom, and a pharmaceutically acceptable carrier.

Another object of the present invention is a pharmaceutical composition comprising an amount of a compound of formula 1 topically effective to treat age-related macular degeneration (AMD) in a mammal such as human suffering therefrom, and a pharmaceutically acceptable carrier.

Another object of the present invention is a pharmaceutical composition comprising an amount of a compound of formula 1 orally effective to treat age-related macular degeneration (AMD) in a mammal such as human suffering therefrom, and a pharmaceutically acceptable carrier.

Another object of the present invention is a pharmaceutical composition comprising an amount of a compound of formula 1 subcutaneously effective to treat age-related macular degeneration (AMD) in a mammal such as human suffering therefrom, and a pharmaceutically acceptable carrier.

Another object of the present invention is a pharmaceutical composition comprising an amount of a compound of formula 1 by injection into the eye effective to treat age-related macular degeneration (AMD) in a mammal such as human suffering therefrom, and a pharmaceutically acceptable carrier.

Another aspect of the invention is a method for treating age-related macular degeneration (AMD) in a mammal such as a human comprising administering a therapeutically effective amount of a compound according to formula 1.

Another object of the present invention is a pharmaceutical composition comprising an amount of a compound of formula 1 effective to treat age-related macular degeneration (AMD) in a mammal such as human suffering therefrom, and a pharmaceutically acceptable carrier in combination with vascular endothelial growth factor (VEGF) inhibitors.

Another aspect of the invention is a method for treating age-related macular degeneration (AMD) in a mammal such as a human comprising administering a therapeutically effective amount of a compound according to formula 1, in combination with vascular endothelial growth factor (VEGF) inhibitors.

Another object of the present invention is a pharmaceutical composition comprising an amount of a compound of formula 1 effective to treat age-related macular degeneration (AMD) in a mammal such as human suffering therefrom, and a pharmaceutically acceptable carrier in combination with a compound selected from the group of vascular endothelial growth factor (VEGF) inhibitors consisting of pegaptinib, vatalinib, pazopanib and other VEGF inhibitors.

Another aspect of the invention is a method for treating age-related macular degeneration (AMD) in a mammal such as a human comprising administering a therapeutically effective amount of a compound according to formula 1, combination with a compound selected from the group of vascular endothelial growth factor (VEGF) inhibitors for example pegaptinib, vatalinib, pazopanib or other VEGF inhibitors.

Another object of the present invention is a pharmaceutical composition comprising an amount of a compound of formula 1 effective to treat age-related macular degeneration (AMD) in a mammal such as human suffering therefrom, and a pharmaceutically acceptable carrier in combination with sphingosine 1-phosphate modulators.

Another aspect of the invention is a method for treating age-related macular degeneration (AMD) in a mammal such as a human comprising administering a therapeutically effective amount of a compound according to formula 1, in combination with sphingosine 1-phosphate modulators.

Another object of the present invention is a pharmaceutical composition comprising an amount of a compound of formula 1 effective to treat age-related macular degeneration (AMD) in a mammal such as human suffering therefrom, and a pharmaceutically acceptable carrier in combination with a compound (sphingosine 1-phosphate modulator) selected from the group consisting of fingolimod, ponesimod (ACT-128800) and 2-amino-2-(5-(5-(3-chloro-4-propoxyphenyl)-1,2,4-oxadiazol-3-yl)benzofuran-2-yl)propane-1,3-diol.

Another aspect of the invention is a method for treating age-related macular degeneration (AMD) in a mammal such as a human comprising administering a therapeutically effective amount of a compound according to formula 1, in combination with a compound (sphingosine 1-phosphate modulators) selected from the group consisting of fingolimod, ponesimod (ACT-128800) and -amino-2-(5-(5-(3-chloro-4-propoxyphenyl)-1,2,4-oxadiazol-3-yl)benzofuran-2-yl)propane-1,3-diol.

Another object of the present invention is a pharmaceutical composition comprising an amount of a compound of formula 1 effective to treat epilepsy in a mammal such as human suffering therefrom, and a pharmaceutically acceptable carrier.

Another aspect of the invention is a method for treating epilepsy in a mammal such as a human comprising administering a therapeutically effective amount of a compound according to formula 1.

Another object of the present invention is a pharmaceutical composition comprising an amount of a compound of formula 1 effective to treat premature ejaculation in a mammal such as human suffering therefrom, and a pharmaceutically acceptable carrier.

Another aspect of the invention is a method for treating premature ejaculation in a mammal such as a human comprising administering a therapeutically effective amount of a compound according to formula 1.

Another aspect of the invention is a method for treating premature ejaculation in a mammal such as a human comprising administering a therapeutically effective amount of a compound according to formula 1 in combination with selective serotonin reuptake inhibitors (SSRI) selected from a group consisting of fluoxetine, paroxetine, sertraline, citalopram, (S)-citalopram and bupropion.

Another object of the present invention is a pharmaceutical composition comprising an amount of a compound of formula 1 effective to treat sexual dysfunction for males and females in a mammal such as human suffering therefrom, and a pharmaceutically acceptable carrier.

Another aspect of the invention is a method for treating sexual dysfunction for males and females in a mammal such as a human comprising administering a therapeutically effective amount of a compound according to formula 1.

Another aspect of the invention is a method for treating male erectile dysfunction in a mammal such as a human comprising administering a therapeutically effective amount of a compound according to formula 1 in combination with sildenafil, tadalafil, and/or vardenafil.

Another object of the present invention is a pharmaceutical composition comprising an amount of a compound of formula 1 effective to treat obesity in a mammal such as human suffering therefrom, and a pharmaceutically acceptable carrier.

Another aspect of the invention is a method for treating obesity in a mammal such as a human comprising administering a therapeutically effective amount of a compound according to formula 1.

Another object of the present invention is a pharmaceutical composition comprising an amount of a compound of formula 1 effective to treat obesity in a mammal such as human suffering therefrom, and a pharmaceutically acceptable carrier in combination with 2-methyl-1-phenylpropan-2-amine (phentermine, phenylethyldimethylamine) and 2,3,4,5-bis-(gemdimethyl-methylenedioxy)-β-D-fructopyranose sulfamate (topiramate or topamax).

Another aspect of the invention is a method for treating obesity in a mammal such as a human comprising administering a therapeutically effective amount of a compound according to formula 1 in combination with 2-methyl-1-phenylpropan-2-amine (phentermine, phenylethyldimethylamine) and 2,3,4,5-bis-(gemdimethyl-methylenedioxy)-β-D-fructopyranose sulfamate (topiramate or topamax).

Another object of the present invention is a pharmaceutical composition comprising an amount of a compound of formula 1 effective to treat obesity in a mammal such as human suffering therefrom, and a pharmaceutically acceptable carrier in combination with naltrexone and bupropion.

Another aspect of the invention is a method for treating obesity in a mammal such as a human comprising administering a therapeutically effective amount of a compound according to formula 1 in combination with naltrexone and bupropion.

Another aspect of the invention is a method for treating bulimia nervosa in a mammal such as a human comprising administering a therapeutically effective amount of a compound according to formula 1.

Another object of the present invention is a pharmaceutical composition comprising an amount of a compound of formula 1 effective to treat bulimia nervosa in a mammal such as human suffering therefrom, and a pharmaceutically acceptable carrier in combination with 2-methyl-1-phenylpropan-2-amine (phentermine, phenylethyldimethylamine) and 2,3,4,5-bis-(gemdimethyl-methylenedioxy)-β-D-fructopyranose sulfamate (topiramate or topamax).

Another aspect of the invention is a method for treating bulimia nervosa in a mammal such as a human comprising administering a therapeutically effective amount of a compound according to formula 1 in combination with 2-methyl-1-phenylpropan-2-amine (phentermine, phenylethyldimethylamine) and 2,3,4,5-bis-(gemdimethyl-methylenedioxy)-β-D-fructopyranose sulfamate (topiramate or topamax).

Another object of the present invention is a pharmaceutical composition comprising an amount of a compound of formula 1 effective to treat bulimia nervosa in a mammal such as human suffering therefrom, and a pharmaceutically acceptable carrier in combination with naltrexone and bupropion.

Another aspect of the invention is a method for treating bulimia nervosa in a mammal such as a human comprising administering a therapeutically effective amount of a compound according to formula 1 in combination with naltrexone and bupropion.

Another aspect of the invention is a method for treating anorexia nervosa in a mammal such as a human comprising administering a therapeutically effective amount of a compound according to formula 1.

Another object of the present invention is a pharmaceutical composition comprising an amount of a compound of formula 1 effective to treat anorexia nervosa in a mammal such as human suffering therefrom, and a pharmaceutically acceptable carrier in combination with 2-methyl-1-phenylpropan-2-amine (phentermine, phenylethyldimethylamine) and 2,3,4,5-bis-(gemdimethyl-methylenedioxy)-β-D-fructopyranose sulfamate (topiramate or topamax).

Another aspect of the invention is a method for treating anorexia nervosa in a mammal such as a human comprising administering a therapeutically effective amount of a compound according to formula 1 in combination with 2-methyl-1-phenylpropan-2-amine (phentermine, phenylethyldimethylamine) and 2,3,4,5-bis-(gemdimethyl-methylenedioxy)-β-D-fructopyranose sulfamate (topiramate or topamax).

Another object of the present invention is a pharmaceutical composition comprising an amount of a compound of formula 1 effective to treat anorexia nervosa in a mammal such as human suffering therefrom, and a pharmaceutically acceptable carrier in combination with naltrexone and bupropion.

Another aspect of the invention is a method for treating anorexia nervosa in a mammal such as a human comprising administering a therapeutically effective amount of a compound according to formula 1 in combination with naltrexone and bupropion.

Another object of the present invention is a pharmaceutical composition comprising an amount of a compound of formula 1 effective to treat smoking cessation in a mammal such as human suffering therefrom, and a pharmaceutically acceptable carrier in combination with bupropion.

Another aspect of the invention is a method for treating smoking cessation in a mammal such as a human comprising administering a therapeutically effective amount of a compound according to formula 1 in combination with bupropion or varinicline.

Another object of the present invention is a pharmaceutical composition comprising an amount of a compound of formula 1 effective to treat depression in a mammal such as human suffering therefrom, and a pharmaceutically acceptable carrier in combination with opiod receptor antagonist such as naltrexone.

Another aspect of the invention is a method for treating depression in a mammal such as a human comprising administering a therapeutically effective amount of a compound according to formula 1 in combination with opiod receptor antagonist such as naltrexone.

Another object of the present invention is a pharmaceutical composition comprising an amount of a compound of formula 1 effective to treat attention deficit hyperactivity disorder (ADHD) in a mammal such as human suffering therefrom, and a pharmaceutically acceptable carrier.

Another aspect of the invention is a method for treating attention deficit hyperactivity disorder (ADHD) in a mammal such as a human comprising administering a therapeutically effective amount of a compound according to formula 1.

Another aspect of the invention is a method of treating ADHD by administering a therapeutically effective amount of a compound according to claim 1 in combination with caffeine, amphetamine, dextroamphetamine, L-lysine-D-amphetamine and methylphenidate Another object of the present invention is a pharmaceutical composition comprising an amount of a compound of formula 1 effective to treat attention deficit disorder (ADD) in a mammal such as human suffering therefrom, and a pharmaceutically acceptable carrier.

Another aspect of the invention is a method for treating attention deficit hyperactivity disorder (ADD) in a mammal such as a human comprising administering a therapeutically effective amount of a compound according to formula 1.

Another aspect of the invention is a method of treating ADD by administering a therapeutically effective amount of a compound of formula 1 in combination with of caffeine, amphetamine, dextroamphetamine, L-lysine-D-amphetamine and methylphenidate Another object of the present invention is a pharmaceutical composition comprising an amount of a compound of formula 1 effective to panic disorder in a mammal such as human suffering therefrom, and a pharmaceutically acceptable carrier.

Another aspect of the invention is a method for treating panic disorder in a mammal such as a human comprising administering a therapeutically effective amount of a compound according to formula 1.

Another object of the present invention is a pharmaceutical composition comprising an amount of a compound of formula 1 effective to hot flashes (vasomotor symptoms) associated with menopause in a mammal such as human suffering therefrom, and a pharmaceutically acceptable carrier.

Another aspect of the invention is a method for treating hot flashes (vasomotor symptoms) associated with menopause in a mammal such as a human comprising administering a therapeutically effective amount of a compound according to formula 1.

Another aspect of the invention is a method of treating hot flashes (vasomotor symptoms) associated with menopause human comprising administering a therapeutically effective amount of a compound according to formula 1 in combination with a selective serotonin reuptake inhibitors (SSRI) selected from the group consisting of dapoxetine, fluoxetine, paroxetine, sertraline, citalopram, (S)-citalopram and bupropion.

Another aspect of the invention is a method for treating obsessive compulsive disorder (OCD) in a mammal such as a human comprising administering a therapeutically effective amount of a compound according to formula 1.

Another aspect of the invention is a method for treating obsessive compulsive personality disorder (OCPD) in a mammal such as a human comprising administering a therapeutically effective amount of a compound according to formula 1.

Another object of the present invention is a pharmaceutical composition comprising an amount of a compound of formula 1 effective to treat autism in a mammal such as human suffering therefrom, and a pharmaceutically acceptable carrier.

Another aspect of the invention is a method for treating autism in a mammal such as a human comprising administering a therapeutically effective amount of a compound according to formula 1.

Another object of the present invention is a pharmaceutical composition comprising an amount of a compound of formula 1 effective to treat Rett's syndrome in a mammal such as human suffering therefrom, and a pharmaceutically acceptable carrier.

Another aspect of the invention is a method for treating Rett's syndrome in a mammal such as a human comprising administering a therapeutically effective amount of a compound according to formula 1.

Another object of the present invention is a pharmaceutical composition comprising an amount of a compound of formula 1 effective to treat migraine in a mammal such as a human suffering therefrom, and a pharmaceutically acceptable carrier.

Another aspect of the invention is a method for treating migraine in a mammal such as a human comprising administering a therapeutically effective amount of a compound according to formula 1.

Another aspect of this invention is a method of treating epilepsy, partial epilepsy, temporal lobes epilepsy, and seizures by administering a pharmaceutically acceptable dose of a compound of formula 1.

Another aspect of this invention is a method of treating epilepsy, partial epilepsy, temporal lobes epilepsy, and seizures by administering a pharmaceutically acceptable dose of a compound of formula 1 is administered with one or more drugs selected from the group consisting of phenyloin, sodium valproate, carbamazepine, phenobarbital, pregabalin, gabapentin, topamax, tiagabine, vigabetrin, oxcarbazepine, levitracetam, eslicarbazepine acetate, and lamotrigine.

Another object of the present invention is a pharmaceutical composition comprising an amount of a compound of formula 1 effective to treat Alzheimer's Disease, frontotemporal dementia, Parkinson's disease, Huntington's disease, schizophrenia, psychosis, cognitive and/or memory impairment (or dysfunction) associated with Alzheimer's disease, schizophrenia, and age-related dementia, psychosis, depression, surgery, comprising administration to a mammal such as human suffering therefrom, and a therapeutically effective amount of at least one of the deuterium-enriched compounds of the present invention or a pharmaceutically acceptable salt thereof as a single agent or in combination with other available medicaments.

It is another object of the present invention to provide a method for treating Alzheimer's Disease, frontotemporal dementia, Parkinson's diseases, Huntington's disease, schizophrenia, psychosis, cognitive impairment, cognitive dysfunction, cognitive decline, memory impairment memory dysfunction or memory decline associated with Alzheimer's disease, schizophrenia, and age-related dementia, Parkinson's disease, psychosis, Huntington disease, depression, surgery, comprising administration to a mammal such as human in need of such treatment a therapeutically effective amount of at least one of the deuterium-enriched compounds of the present invention or a pharmaceutically acceptable salt thereof as a single agent or in combination with other available medicaments.

Another object of the present invention is a pharmaceutical composition comprising an amount of a compound of formula 1 effective to treat nociception or pain associated with or attributable to any of the foregoing conditions in a mammal such as a human suffering therefrom, and a pharmaceutically acceptable carrier.

Another aspect of the invention is a method for treating nociception or pain associated with or attributable to any of the foregoing conditions in a mammal such as a human comprising administering a therapeutically effective amount of a compound according to formula 1.

Another object of the present invention is a pharmaceutical composition comprising an amount of a compound of formula 1 effective to treat anxiety, generalized anxiety disorder and panic disorders in a mammal such as human suffering therefrom, and a pharmaceutically acceptable carrier.

Another aspect of the invention is a method for treating anxiety, generalized anxiety disorder and panic disorders in a mammal such as a human comprising administering a therapeutically effective amount of a compound according to formula 1.

Another object of the present invention is a pharmaceutical composition comprising an amount of a compound of formula 1 effective to treat depression, major depressive disorder and bipolar depression in a mammal such as human suffering therefrom, and a pharmaceutically acceptable carrier.

Another aspect of the invention is a method for treating depression, major depressive disorder and bipolar depression in a mammal such as a human comprising administering a therapeutically effective amount of a compound according to formula 1.

Another object of the present invention is a pharmaceutical composition comprising an amount of a compound of formula 1 effective to treat sleep disorders and/or insomnia in a mammal such as a human suffering therefrom, and a pharmaceutically acceptable carrier.

Another aspect of the invention is a method for treating sleep disorders and/or insomnia in a mammal such as a human comprising administering a therapeutically effective amount of a compound according to formula 1.

Another object of the present invention is a pharmaceutical composition comprising an amount of a compound of formula 1 effective to treat eating disorders, anorexia nervosa, and/or bulimia in a mammal such as a human suffering therefrom, and a pharmaceutically acceptable carrier.

Another aspect of the invention is a method for treating eating disorders, anorexia nervosa, and/or bulimia in a mammal such as a human comprising administering a therapeutically effective amount of a compound according to formula 1.

Another object of the present invention is a pharmaceutical composition comprising an amount of a compound of formula 1 effective to treat stress-related somatic disorders and sympathetic dystrophy such as shoulder and hand syndrome in a mammal such as a human suffering therefrom, and a pharmaceutically acceptable carrier.

Another aspect of the invention is a method for treating stress-related somatic disorders and sympathetic dystrophy such as shoulder and hand syndrome in a mammal such as a human comprising administering a therapeutically effective amount of a compound according to formula 1.

Another object of the present invention is a pharmaceutical composition comprising an amount of a compound of formula 1 effective to treat insomnia and migraine in a mammal such as a human suffering therefrom, and a pharmaceutically acceptable carrier.

Another object of the present invention is a pharmaceutical composition comprising an amount of a compound of formula 1 effective to treat alcohol withdrawal and migraine in a mammal such as a human suffering therefrom, and a pharmaceutically acceptable carrier.

Another object of the present invention is a pharmaceutical composition comprising an amount of a compound of formula 1 effective to treat fibromyalgia and migraine in a mammal such as a human suffering therefrom, and a pharmaceutically acceptable carrier.

Another object of the present invention is a pharmaceutical composition comprising an amount of a compound of formula 1 effective to treat vascular disorders such as angina and migraine in a mammal such as a human suffering therefrom, and a pharmaceutically acceptable carrier.

Another aspect of the invention is a method for treating vascular disorders such as angina and migraine in a mammal such as a human comprising administering a therapeutically effective amount of a compound according to formula 1.

All processes for synthesizing the deuterium-enriched compounds and novel intermediates are also included in the invention.

BACKGROUND OF THE INVENTION

Neurotransmitter serotonin or 5-Hydroxytryptamine (5-HT) is abundantly distributed in the central nervous system, including hippocampus and frontal cortex. The 5-HT receptors are a family of G-protein coupled receptors, characterized with 7-transmembrane helices and presently have fourteen known receptor subtypes, some of which exist as multiple splice variants [D. L. Murphy, A. M. Andrews, C. H. Wichems, Q. Li, M. Tohda and B. Greenberg, J. Clin. Psychiatry, 1998, 59 (suppl. 15), 4]. Serotonin (5-HT) influences a number of physiological functions and is implicated in a large number of central nervous system disorders, neurodegenerative diseases [W. E. Childers, Jr. and A. J. Robichaud, Ann. Rep. Med. Chem. 2005, 40, 17 herein incorporated by reference in its entirety] and other diseases.

One of the most actively studied 5-HT receptor subtypes is 5-HT$_{1A}$, a 421 amino acid protein coded on human chromosome 5 by an intronless gene. 5-HT$_{1A}$ receptors are expressed in the central nervous system with highest density in the dorsal and median raphe nuclei as well as in the hippocampus. High density is also seen in the frontal cortex, entorhinal cortex, amygdale, and septum. 5-HT$_{1A}$ agonists and partial agonists have been implicated and have demonstrated effectiveness in the treatment of anxiety and depression in the clinic. Partial agonists of the 5-HT$_{1A}$ receptor mediate antidepressant activity through an increase in serotonergic neurotransmission. Although the mechanism of action is not yet fully understood, there is substantial evidence that the physiological and behavioral responses are achieved following desensitization of the 5-HT$_{1A}$ receptor-mediated response.

5-HT$_{1A}$ receptor partial agonists have been found to be useful in the treatment of various central nervous system diseases and disorders including anxiety, general anxiety disorders, depression, major depressive disorders, ADHD, ADD, schizophrenia, psychosis, panic disorders, social phobia, hot flashes associated with menopause, obesity, bulimia nervosa, anorexia nervosa, smoking cessation, schizophrenia, psychosis, sexual dysfunctions, premature ejaculation, memory and cognitive dysfunction, mild cognitive impairment associated with Alzheimer's diseases, Parkinson's diseases, Parkinson's disease psychosis, Huntington diseases and others.

According to the U.S. National Institute of Mental Health, generalized anxiety disorder and depression are the most prevalent mental illnesses. Most of the drugs used for treating anxiety and depression and stress related panic disorder suffer from troublesome side effects. Selective serotonin reuptake inhibitors (SSRIs) and the more recently developed serotonin nonadrenaline reuptake inhibitors (SNRIs) exert their effects by increasing neurotransmitter availability and transmission. Another class of drugs used for the short-term relief of anxiety is benzodiazepines. These sedating agents are controlled substances because of their addictive properties and can be lethal when used in combination with alcohol.

It is generally known that 5-HT$_{1A}$ receptor is involved in psychiatric disorders such as anxiety and depression (Fletcher, A.; Cliffe, I. A.; Dourish, C. T., Silent 5-HT$_{1A}$ receptor antagonists: utility as research tools and therapeutic agents. Trends Pharmacol. Sci. 1993, 14, 441-448, herein incorporated by reference; Hamon, M, Neuropharmacology of anxiety: perspective and prospects. Trends Pharmacol. Sci. 1994, 15, 36-39, herein incorporated by reference; Blier, P; Montigny, C.; Current advances and trends in the treatment of depression. Trends Pharmacol. Sci. 1994, 15, 220-226, herein incorporated by reference; Lo'pez-Rodriguez, M. L.; Rosado, M. L.; Benhamu, B; Morcillo, M. J; Sanz, A. M.; Orensanz, L.; Beneitez, M. E.; Fuentes, J. A.; Manzanares, J, Synthesis and structure activity relationships of a new model of arylpiperazines. 1.2-[[4-(o-Methoxyphenyl)piperazin-1-yl]methyl]-1,3-dioxoperhydromidazo[1,5-a]pyridine: A selective 5-HT$_{1A}$ receptor agonist. J. Med. Chem. 1996, 39, 4439-4450, herein incorporated by reference; Becker, O M.; Dhanoa, D S.; Marantz, Y,; Chen, D.; Shacham, S.; Cheruku, S.; Heifetz, A.; Mohanty, P.; Fichman, M.; Sharadendu, A.; Nudelman, R.; Kauffman, M; Noiman, S. An integrated in silico 3D model-driven discovery of a novel, potent and selective Amidosulfonamide 5-HT$_{1A}$ agonist (PRX-00023) for the treatment of anxiety and depression. J. Med. Chem. 2006, 49, 3116-3135, herein incorporated by reference). Buspirone, an arylpiperazine that has shown high affinity for the 5-HT$_{1A}$ receptor, was the first drug to be approved for clinical use for the treatment of anxiety and depression (Taylor, D P.; Moon, S. L. Buspirone and related compounds as alternative anxiolytics. Neuropeptides 1991, 19, 15-19; Levy, A. D.; van der Kar, L. D.; Endocrine and receptor pharmacology of serotoninergic anxiolytics, antipsychotics and antidepressants. Life Sci. 1992, 51, 83-94). However, buspirone has poor receptor selectivity, poor oral bioavailability, duration of action, and slow onset. Buspirone has high affinity for alpha-1 (Raghupathi, R. K.; Rydelek-Fitzgerald, L.; Teitler, M; Glennon, R. A. Analogs of the 5-HT$_{1A}$ serotonin antagonist 1-(2-Methoxyphenyl)-4-[4-(2-phthalimidobutyl)piperazine] with reduced alpha-1 adrenergic affinity. J. Med. Chem. 1991, 34, 2633-2638). The high affinity of buspirone for the alpha-1 adrenergic receptor is attributable to its adverse effect of orthostatic hypotension (decreased blood pressure).

Effects of a 5-HT$_{1A}$ partial agonist PRX-00023 on anxiety and depression including general anxiety disorders and major depressive disorders from a randomized, double-blind, placebo controlled trial conducted in 311 subjects have shown significant potential for the treatment of general anxiety disorders and major depressive disorders and with fewer side effects (Rickels, K.; Mathew S.; Banov, M. D; Zimbroff, D. L.; Oshana, S.; Parsons, E. C. Jr.; Donahue, S. R.; Kauffman, M.; Iyer, G. R.; Reinhard, J. F. Jr., J. Clin. Psychopharmacol. 2008, 28(2), 235-9, herein incorporated by reference).

Serotonin or 5-Hydroxytryptamine receptor subtype 1A ($5-HT_{1A}$) offers a valuable and efficacious therapeutic approach to the treatment of anxiety and major depression (Blier, P.; Ward, N. M. Is there a role for $5-HT_{1A}$ agonists in the treatment of depression. Biol. Psychiatry. 2003, 53(3), 193-203, herein incorporated by reference).

Vilazodone was approved for the treatment of major depressive disorder by the US FDA in 2011 (Ann. Rep. Med. Chem. 2012, 47, 558; Frampton, J E., CNS Drugs 2011, 25, 615; Laughren, T. P. et. al. J. Clin. Psychiatry 2011, 72, 1166, herein incorporated by reference). Major depressive disorder (MDD) is characterized by persistent low mood, sadness, loss of interest in previously enjoyed activities, feelings of guilt or worthlessness, and thoughts of death or suicide. Nearly 15% of the United States population will experience MDD in their lifetime, with more prevalence in women. Vilazodone (Viibryd) is a $5-HT_{1A}$ partial agonist and dual serotonin reuptake inhibitor. Vilazodone is a novel antidepressant that combines potent serotonin reuptake inhibition ($IC_{50}$=0.2 nM) with high affinity for $5-HT_{1A}$ receptor ($IC_{50}$=0.5 nM) and partial agonist functional activity for $5-HT_{1A}$ receptor. Vilazodone demonstrated efficacy in preclinical rat and mice models of depression (Page, M. E.; Cryan, J. F.; Sullivan, A.; Dalvi, A; Saucy, B.; Manning, D. R.; Lucki, I. *J. Pharmacol. Exp. Ther.* 2002, 302, 1220). As with all approved antidepressant drugs in the United States, vilazodone has a black box warning describing the increased risk of suicidal thinking and behavior in children, adolescents, and young adults.

Current antidepressants including selective serotonin reuptake inhibitors, serotonin noradrenaline reuptake inhibitors and tricyclic antidepressants-all modulate monoamine levels and have limitations that include a lack of effectiveness in a substantial proportion of patients. Nearly 50% of patients have depression that is difficult to treat and need drugs with new modes of action. New antidepressants that target the kappa-opioid receptor could be valuable for patients suffering from stress-induced component in their illness. Patients with anxiety and depression have heightened sensitivities to stress exposure, and the endogenous dynorphin opioid peptides that are released during stress act at kappa-opioid receptors. In preclinical models, kappa-opioid receptor antagonists effectively reduce the anxiety-like and depression-like behaviors caused by stress exposure.

Recently, a clinical candidate ALKS-5461, a combination therapy composed of a selective mu-opioid receptor antagonist, samidorphan (ALKS33), and a mixed kappa-opioid receptor antagonist and a mu-opiod receptor agonist, buprenorphine (that is already approved for the treatment of pain and opioid addiction), have shown positive results in Phase 2 clinical trials (ClinicalTrials.gov Identifier NCT01500200) for the treatment of patients with major depressive disorders (MDD) (http://clinicaltrials.gov/ct2/show/NCT01500200) who do not respond to current therapies. Buprenorphine has weak mu-opiod receptor (where morphine and oxycodone act) agonist activity, there are risks of sedation and addiction. So combination of buprenorphine with a mu-opioid antagonist offers the formulation superior functional selectivity.

The compounds of the present invention of formula 1 have been found to be potent $5-HT_{1A}$ partial agonists and offer a novel, safer and effective treatment when administered alone or in combination with existing or new therapies such as vilazodone and ALKS-5461 respectively for the treatment of anxiety, depression and related major depressive disorders.

As can be seen from the package insert of the atypical antipsychotic drug, Aripiperazole (Abilify), it has been approved as a tablet, oral formulation and as an injectable agent by the US. FDA for the use of various central nervous system diseases and disorders including schizophrenia, acute treatment of manic or mixed episodes associated with bipolar I disorder as monotherapy or as an adjunct lithium or valproate, maintenance treatment of bipolar I disorder both as monotherapy or as an adjunct lithium or valproate, adjunctive treatment of major depressive disorders (MDD), treatment of irritability associated with autistic disorder, acute treatment of agitation associated with schizophrenia or bipolar I disorder (intramuscular injection) or bipolar mania.

Aripiprazole has been shown to have partial agonist functional activity at $5-HT_{1A}$ receptor with binding affinity (Ki) of 5.6 nM and varied biological activity at other 5-HT receptor subtype including Ki of 832 nM for $5-HT_{1B}$ receptor, Ki of 65 nM for $5-HT_{1D}$, Ki of 8.7 nM for $5-HT_{2A}$ receptor, Ki of 0.36 nM at $5-HT_{2B}$ receptor, Ki of 22.4 nM at $5-HT_{2C}$ receptor, Ki of 628 nM at $5-HT_3$, Ki of 1240 nM at $5-HT_{5A}$ receptor, and Ki of 642 nM at $5-HT_6$ receptor. Aripiperazole also shows varied degree of activity for dopamine receptors, $D_1$ receptor Ki of 1170 nM, $D_2$ receptor Ki of 1.6 nM and acts as partial agonist, $D_3$ receptor Ki of 5.4 nM, $D_4$ receptor Ki of 514 nM and $D_5$ receptor Ki of 2130 nM. Aripiperazole has a warning of increased risk of suicidal thoughts and behavior, and early patients with dementia-related psychosis treated with antipsychotic drugs are at an increased risk of death.

Lurasidone, an atypical antipsychotic agent, was approved in the United States in 2010 for the treatment of schizophrenia (Ann. Rep. Med. Chem. 2011, 46, 473; Hopkins, C. R. ACS Chem. Neurosci. 2011, 2, 58; Citrome, L. Int. J. Clin. Prac. 2011, 65, 189). Lurasidone has high affinity for $5-HT_{1A}$ receptor ($IC_{50}$ 6 nM), dopamine $D_2$ receptor (Ki 2 nM) and $5-HT_{2A}$ ($IC_{50=2}$ nM) (Ishibashi, T. et. al. *J. Pharmacol. Exp Ther.* 2010, 334, 171). Lurasidone is also a partial agonist at $5-HT_{1A}$ receptor which produces beneficial cognitive properties. Lurasidone has shown efficacy in preclinical behavioral model of psychosis, depression and anxiety. Lurasidone also has a black box warning for increased mortality in elderly patients with dementia-related psychosis. Schizophrenia is a debilitating mental disorder that affects 1% of the population worldwide.

$5-HT_{1A}$ partial agonists have been shown to have activity for the treatment of Attention deficit hyperactivity disorder (ADHD) particularly in combination with norepinephrine reuptake inhibitors (Gray, D. L.; Xu, W.; Campbell, B. M; Dounay, A. B.; Barta, N.; Boroski, S.; Denny, L.; Evans, L.; Stratman, N.; Probert, Al. Discovery and pharmacological characterization of arylpiperazine and piperadine ethers as dual acting norepinephrine reuptake inhibitors and $5-HT_{1A}$ partial agonists. Bioorg. Med. Chem. Lett. 2009, 19 (23), 6604-6607, herein incorporated by reference).

Since the FDA approval of buspirone for the treatment of generalized anxiety disorders (GAD), numerous studies have examined the safety and efficacy of buspirone for patients with not only generalized feeling of anxiety, but also panic disorder, major depressive disorder, obsessive-compulsive disorder, body dysmorphic disorder, social phobia, post-traumatic stress disorder, SSRI-induced adverse events, dementia, behavioural disturbances, attention deficit-hyperactivity disorder (ADHD), and tobacco dependency. Apter and Allen reviews the growing body of research relating to new therapeutic uses of buspirone (Apter, J. F.; Allen, L. A. Buspirone: Future directions. J. Clin. Psychopharmacol. 1999, 19:86-93).

The $5-HT_{1A}$ agonists are potentially safer and more effective therapeutic drugs for the treatment of anxiety disorders including, General Anxiety Disorder (GAD), Panic Disorder (PD), Post-Traumatic Stress Disorder (PTSD), Social Phobia (SP), Health Anxiety (Hypochondriasis), depression, major depressive disorders, unipolar depression, bipolar I depression disorder, bipolar II depression disorder, treatment-resistant depression, single episodic and recurrent major depressive disorders, depression in the medically ill, attention deficit hyperactivity disorder (ADHD), attention deficit disorder (ADD), Obsessive-Compulsive Disorder (OCD), Obsessive-Compulsive Personality Disorder (OCPD), Autism Spectrum Disorder (ASD), schizophrenia, psychosis, epilepsy, seizures, hot flashes due to menopause, age-related macular degeneration (AMD), premature ejaculation, male erectile dysfunction, sexual dysfunction, obesity, eating disorders, bulimia nervosa, anorexia nervosa, angina, smoking cessation, migraine, pain, nociception, sleep disorders, autism, Rett's syndrome, cyclothymic disorder, neural injury, neurodegenerative diseases, Parkinson's disease, Parkinson's disease psychosis, Huntington disease, Alzheimer's disease, frontotemporal dementia, cognitive impairment associated with age-related dementia, Alzheimer's disease, schizophrenia, psychosis, depression, surgery or any medical illness.

The $5\text{-}HT_{1A}$ receptors have also been implicated in the pathophysiology of age-related macular degeneration (AMD), epilepsy and seizures and other neurodegeneration diseases and disorders. $5\text{-}HT_{1A}$ receptor modulators (agonist or partial agonist) have shown potential for the treatment of age-related macular degeneration (AMD), epilepsy, seizures, premature ejaculation, obesity, Parkinsons' disease, psychosis and other central nervous system diseases mentioned below.

The $5\text{-}HT_{1A}$ (5-hydroxytryptamine or serotonin) receptor agonists, partial agonists or antagonists are neuroprotective agents. $5\text{-}HT_{1A}$ agonists have been shown to be neuroprotective agents against excitotoxic neuronal damage in animal models of central nervous system injury such as stroke and traumatic brain injury (Mauler, F.; Horvath, E., J. Cereb. Blood Flow Metab. 2005, 25, 451-45; Ramos, A. J., The $5\text{-}HT_{1A}$ receptor agonist, 8-OH-DPAT, protects neurons and reduces astroglial reaction after ischemic damage caused by cortical devascularization. Brain Res. 2004, 1030, 201-220, herein incorporated by reference). Several putative mechanisms that have been proposed include inhibition of caspase 3 and activation of the mitogen-activated protein kinase (MAPK) signaling pathway (Adayev et. al., Biochim. Biophys. Acta., 2003, 1640, 85-96) which results in increased expression of anti-apoptotic proteins (e.g., XIAP, BCL-2, and BCL-$X_L$) (Hsiung et. al., J. Neurochem., 2005, 95, 1653-1666).

As is shown by Collier et. al. from Alcon (Collier et al. Investigative Ophthalmology & Visual Science, (IOVS), 2011, 52 (5), 2118-2126, herein incorporated by reference) the $5\text{-}HT_{1A}$ receptor agonist may offer a novel approach to retinal neuroprotection for retinal disorders such as age-related macular degeneration (AMD). Oxidative stress and inflammation are thought to play pivotal roles in the etiology of age-related macular degeneration (Kanda et. al. Br. J. Ophthalmol. 2008, 92, 448-450; Beatty et. al. Surv. Ophthalmol. 2000, 45, 115-134; Winkler et. al. Mol. Vis. 1999, 5, 32-42); Shen et. al. Histol. Histopathol. 2007, 22, 1301-1308, herein incorporated by reference). Topical ocular application with 1.75% of the $5\text{-}HT_{1A}$ agonist AL-8309B once or twice daily provided protection from photo-oxidative damage to the retina (Collier et al). This is a very useful, convenient and less painful route of administration for the potential treatment of retinal disorders such as macular degeneration. The current available treatments require injection of VEGF inhibitors directly into the eye, every four to six weeks. A clinical trial evaluating the safety and efficacy of topically administered $5\text{-}HT_{1A}$ partial agonist, AL-8309B, for the treatment of advanced nonexudative age-related macular degeneration (geographic atrophy) is under way (Geographic atrophy treatment evaluation. ClinicalTrials.gov Identifier: NCT00890097).

In addition, the $5\text{-}HT_{1A}$ receptor has been implicated in the pathophysiology of epilepsy. The neurotransmitter 5-HT (serotonin) assists communication of nerve cells. Previous research studies have shown that 5-HT activity may be diminished in the CNS areas of the brain where seizures occur. Research studies also suggest that increase in activity at the 5-HT receptor site on the nerve cells may help prevent seizures. The 5-HT agonists such as $5\text{-}HT_{1A}$ receptor agonists or partial agonists may reduce epileptic seizures. A $5\text{-}HT_{1A}$ partial agonist PRX-00023 (Becker, O M.; Dhanoa, D S.; Marantz, Y,; Chen, D.; Shacham, S.; Cheruku, S.; Heifetz, A.; Mohanty, P.; Fichman, M.; Sharadendu, A.; Nudelman, R.; Kauffman, M; Noiman, S. An integrated in silico 3D model-driven discovery of a novel, potent and selective Amidosulfonamide $5\text{-}HT_{1A}$ agonist (PRX-00023) for the treatment of anxiety and depression. J. Med. Chem. 2006, 49, 3116-3135, herein incorporated by reference), is undergoing Phase II clinical trials for the treatment of epilepsy specifically localization-related epilepsy (http://clinicaltrials.gov/ct2/show/NCT01281956).

The $5\text{-}HT_{1A}$ receptors have also been implicated in the pathophysiology underlying premature ejaculation. It may also have a direct or indirect role in other sexual dysfunction such as erectile dysfunction or sexual desire. Premature ejaculation (PE) is the most common form of male sexual dysfunction affecting nearly 40% of men globally. Premature ejaculation (PE) is a common sexual dysfunction in men that is characterized by a short time to ejaculation and a lack of control over ejaculation. PE is associated with distress for men and their partners. Lack of knowledge about the etiology of PE and lack of approved treatments might contribute to its under-diagnosis and under-treatment. Ejaculation is a reflux comprising different sensory pathways, motor centers, and nerve pathways regulated by serotonin and dopamine. The pathophysiology of PE includes decreased serotonin neurotransmission and $5\text{-}HT_{1A}$ receptor hypersenstivity. Selective serotonin reuptake inhibitors (SSRIs) commonly used as antidepressants are often used to treat PE because of their frequent side effect delayed ejaculation. Animal studies have shown that SSRIs block presynaptic membranes of 5-HT transporters, resulting in higher serotonin (5-HT) levels in the synaptic cleft. The 5-HT then binds to $5\text{-}HT_{1A}$ receptor and $5\text{-}HT_{2C}$ to delay ejaculation. The most commonly used SSRIs to treat PE include the long-acting agents, fluoxetine, paroxetine, sertraline, and citalopram. Several clinical studies have shown that chronic use of SSRIs results in prolonged intravaginal ejaculatory latency time in men with PE. However, chronic use of SSRIs is associated with undesirable sexual side effects and withdrawal symptoms upon discontinuation. Dapoxetine hydrochloride is the recent serotonin modulator approved in 2011 by the US FDA for the oral on-demand treatment of PE in men between 18-64 years of age. Dapoxetine HCl is a short-acting SSRI. It is differentiated from the existing SSRI treatments for PE because it can be dosed on an as-needed basis (Ann. Rep. Med. Chem. 2010, 45, 488; Sorbera, L. A., et. al. Drugs Future 2004, 29, 1201; Hellstrom, W. J. G. et. al. Neuropsychiatr. Dis. Treat., 2009, 5, 37, herein incorporated by reference). The most common adverse events with dapoxetine included nausea, diarrhea, headache, dizziness, and somnolence.

The organic factors involved in PE are not well understood but serotonin (5-hydroxytryptamine, 5-HT) is important at the level of the central nervous system in the complex regulatory mechanisms involved in ejaculation. Current available medicines for PE in addition to off-label use of SSRIs are PDE-5 inhibitors and topical anaesthetics, which have shown variable efficacy and tolerability. Drugs for treating PE will continue to develop as the understanding of ejaculation expands, including the role of central neurotransmitters as future targets to delay ejaculation. The neurotransmitter 5-HT appears to be a key mediator in the neurophysiology of ejaculation (Giuliano et al. Eur. Urol. 2005, 48, 408-417). 5-HT neurons express somatodendritic autoreceptors (including $5\text{-HT}_{1A}$ receptors present in the mesencephalic and medullary raphe nuclei), presynaptic autoreceptors ($5\text{-HT}_{1B}$ and $5\text{-HT}_{1D}$), 5-HT signalling receptors (e.g. $5\text{-HT}_{2C}$), and 5-HT reuptake transporters, each of which mediate different effects on cellular activation and 5-HT signaling Waldinger et al. Behav. Brain Res. 1998, 92, 111). In general, activation of $5\text{-HT}_{1A}$ autoreceptors decreases 5-HT release by the pre-synaptic neurone, providing a negative-feedback mechanism for 5-HT neurotransmission (Giouliano et al. Eur. Urol. 2006, 50, 454-66). Signal transduction through $5\text{-HT}_{1A}$ and $5\text{-HT}_{2C}$ receptors plays a key role in regulating ejaculation at the central level (Ahlenius, et. al. Neurochem Res. 1997, 22, 1065-70). Activation of postsynaptic $5\text{-HT}_{2C}$ or $5\text{-HT}_{1B}$ receptors prolongs ejaculatory latency, whereas activation of presynaptic $5\text{-HT}_{1A}$ autoreceptors, which inhibits 5-HT release, decreases ejaculatory latency. It was suggested that PE might be associated with the presence of low synaptic levels of 5-HT in regions of the CNS that modulate ejaculation, possibly because of variations in 5-HT receptor sensitivity. It seems that increasing central 5-HT is a relevant pharmacological approach to treat premature ejaculation (PE).

$5\text{-HT}_{1A}$ receptors play important role in Parkinson's disease and schizophrenia. Specifically, $5\text{-HT}_{1A}$ receptors seem to be a promising target for alleviating antipsychotic-induced extrapyramidal side effects (EPS) and cognitive/affective disorders in schizophrenia. In the treatment of patients with Parkinson's disease, $5\text{-HT}_{1A}$ agonists are expected to improve not only affective symptoms (e.g., anxiety and depression), but also the core parkinsonian symptoms as well as antiparkinsonian agents-induced side effects (e.g., L-DOPA-induced dyskinesia). The review of therapeutic mechanisms mediated by $5\text{-HT}_{1A}$ receptors in schizophrenia and Parkinson's disease are reported (Ohno et al. CNS Neuroscience and Therapeutics, 2011, 17 (1), 58-65, herein incorporated by reference). There is a potential promising use of new $5\text{-HT}_{1A}$ agonists in the treatment of Parkinson's disease, schizophrenia and psychosis related to these brain disorders.

$5\text{-HT}_{1A}$ receptor agonists have also been implicated in the treatment of obesity and related eating disorders such as bulimia nervosa and anorexia nervosa. Peripheral injection of serotonin reduces food intake and specifically decreases fat intake. Since the majority of serotonin (5-HT) is present in the gastrointestinal tract, it is highly likely that 5-HT receptors in this tissue play an important role in the regulation of food intake in response to enteral signals or to the rate of gastric emptying.

Belviq (Lorcaserin HCl) has recently been approved by the U.S FDA for the treatment of obesity and controlling eating and/or food intake. As is clear from its package insert, Belviq decreases food consumption and promotes satiety by activating $5\text{-HT}_{2C}$ receptor in the brain. Activation of 5-HT receptors may help overweight or obese patients eat less and feel full. The exact mechanism of action is not clear.

As seen from its package insert Qsymia® (phentermine and topiramate) has been approved by the U.S. FDA in 2012 for treatment of obesity. Qsymia is a combination of phentermine, a sympathomimetic amine anorectic, and topiramate extended-release form, an antiepileptic drug approved as an adjunct to a reduced calorie diet and increased physical activity for chronic weight management in adults. Phentermine releases serotonin (5-HT), dopamine and norepinephrine at clinically relevant doses (Rothman, R. B., et. al. Synapse, 2001, 39 (1), 32-4). Phentermine acts on the hypothalamus to stimulate the release of norepinephrine that signal reduction in appetite.

Contrave has completed pivotal clinical trials (Phase III) for the treatment of obesity and a New Drug Application has been submitted and has been reviewed by the U.S. FDA (http://www.orexigen.com/about-orexigen.html). Contrave is a combination of bupropion and naltrexone. Bupropion increases the dopamine activity in the brain which leads to reduction in appetite and increase in energy expenditure by enhancing neuron activity. Bupropion is a norepinephrine and dopamine reuptake inhibitor. Naltrexone on the other hand is an opioid receptor antagonist and prevents the feedback inhibition of neurons. Thus, Contrave may regulate activity in the dopamine reward system of the brain which helps control food cravings, overeating behaviors and increase metabolism.

The $5\text{-HT}_{1A}$ receptors in medial prefrontal cortex (mPFC) are involved in the modulation of dopaminergic activity (Diaz-Mataix, L.; Scorza, M. C.; Borotolozzi, A.; Toth, M.; Celada, P.; Artigas, F. The Journal of Neuroscience, 2005, 25(47), 10831-10843). The results published in this paper showed that the activation of medial prefrontal cortex (mPFC) enhances the activity of ventral tegmental area (VTA) DA neurons and mesocortical dopamine release. The highly selective $5\text{-HT}_{1A}$ agonist BAYx3702 was found to increase the firing rate and burst firing of dopamine (DA) neurons in the ventral tegmental area (VTA) and DA release in the VTA and mPFC. The increase in DA release in both areas was potentiated by nomifensine coperfusion. The application of BAY in rat and mouse mPFC by reverse dialysis increased local extracellular DA at a low concentration of 3 micromolar and reduced it at a higher concentration (30 micromolar). Both effects disappeared in a $5\text{-HT}_{1A}$ knock-out mice.

Buspirone (Buspar), a $5\text{-HT}_{1A}$ partial agonist has been tested clinically for smoking cessation. Early open-label studies suggested that buspirone increased quit rates and reduced withdrawal symptoms (Hilleman D. E.; Mohiuddin, S. M; Del Corte, M. G.; Sketch, M. H. Sr., Effect of buspirone on withdrawal symptoms associated with smoking cessation. Arch. Intern. Med. 1992, 152 (2), 350-352; Robinson, M. D.; Smith, W. A.; Cederstrom, E. A.; Sutherland, D. E.; Buspirone effect on tobacco withdrawal symptoms: a pilot study. J. Am. Board Fam. Pract., 1991, 4(2), 89-94; West, R.; Hajek, P.; McNeill, A. Effect of buspirone on cigarette withdrawal symptoms and short term abstinence rates in a smoker's clinic. Psychopharmacology, 1991, 104 (1), 91-96).

In addition, as seen from its package insert, Zyban® (bupropion hydrochloride) has been approved by the U.S. FDA for use in smoking cessation programs. Bupropion HCl is a $5\text{HT}_{1A}$ partial agonist as shown by Mansari et al. (El Mansari, M.; Ghanbari, R.; Janssen, S.; Blier, P., Sustained administration of bupropion alters the neuronal activity of serotonin, norepinephrine but not dopamine neurons in the rat brain. Neuropharmacology, 2008, 55 (7), 1191-98).

Hot flashes associated with menopause occur in up to 75% of women and can persist up to five years, or even longer in some women. Hot flashes are not life threatening but the symptoms can be very bothersome, causing discomfort, embarrassment and disruption of sleep. The U.S. FDA has approved the antidepressant paroxetine for the treatment of moderate to severe hot flashes (vasomotor symptoms) associated with menopause (http://www.fda.gov/NewsEvents/Newsroom/PressAnnouncements/ucm359030.htm). Paroxetine mesylate (trade name: Brisdelle), a selective serotonin reuptake inhibitor (SSRI), is currently the only non-hormonal treatment for hot flashes approved by the FDA. There are various FDA-approved treatments for hot flashes but all contain either estrogen alone or estrogen plus a projestin. The mechanism by paroxetine (Brisdelle) reduces hot flashes is unknown. The most common side effect in patients treated with paroxetine were headache, fatigue and nausea/vomiting. All antidepressant agents including paroxetine have a boxed warning about an increased risk of suicide in children and young adults. Of particular concern to menopause women is the potential for weight gain and sexual dysfunction, which are adverse effects associated with SSRI and SNRIs. Paroxetine also has activity at the 5-HT$_{1A}$ and other 5-HT receptors and therefore, potent and selective 5-HT$_{1A}$ partial agonist will offer a significant advantage over current therapies including paroxetine.

Trazodone, a 5-HT$_{1A}$ partial agonist approved for the treatment of anxiety (Haria, M., et al. Trazadone. A review of its pharmacology, therapeutic use in depression and therapeutic potential in other disorders. Drugs Aging, 1994, 4, 331-55), is also used for the treatment of insomnia (Nierenberg, A. A., et al. Trazodone for antidepressant-associated insomnia, Am J. Psychiatry, 1994, 151, 1069-72); Kaynak, H. et al. The effects of Trazodone on sleep in patients treated with stimulant antidepressants., Sleep Med. 2004, 5, 15-20), Fibromyalgia (Morillas-Arques, P., et. al. Trazodone for the treatment of fibromyalgia: an open label, 12 week study, BMC Musculoskeletal Disorders, 2010, 11, 204, http://www.biomedcentral.com/1471-2474/11/204) and alcohol withdrawal. Borras, L; de Tamary, P.; Constant, E-L.; Huguelet, P.; Eytan, A. Successful treatment of alcohol withdrawal with Trazodone. Pharmacopsychiatry, 2006, 39 (6), 232).

DETAILED DESCRIPTION OF THE INVENTION

The present invention relates to deuterium-enriched alkylsulfonamides and their derivatives as shown in formula 1, their pharmaceutically acceptable salts, compositions and uses thereof as therapeutic agents for the prevention and treatment of anxiety disorders including, General Anxiety Disorder (GAD), Panic Disorder (PD), Post-Traumatic Stress Disorder (PTSD), Social Phobia (SP), Health Anxiety (Hypochondriasis), depression, major depressive disorders, unipolar depression, bipolar I depression disorder, bipolar II depression disorder, treatment-resistant depression, single episodic and recurrent major depressive disorders, depression in the medically ill, attention deficit hyperactivity disorder (ADHD), attention deficit disorder (ADD), Obsessive-Compulsive Disorder (OCD), Obsessive-Compulsive Personality Disorder (OCPD), Autism Spectrum Disorder (ASD), schizophrenia, psychosis, epilepsy, seizures, hot flashes due to menopause, age-related macular degeneration (AMD), premature ejaculation, male erectile dysfunction, sexual dysfunction, obesity, eating disorders, bulimia nervosa, anorexia nervosa, angina, migraine, pain, nociception, sleep disorders, insomnia, fibromyalgia, alcohol withdrawal, autism, Rett's syndrome, cyclothymic disorder, neural injury, neurodegenerative diseases, Parkinson's disease, Parkinson's disease psychosis, Huntington disease, Alzheimer's disease, frontotemporal dementia, cognitive impairment associated with age-related dementia, Alzheimer's disease, schizophrenia, psychosis, depression, pain or discomfort associated with surgery and pain or discomfort associated with medical illness,

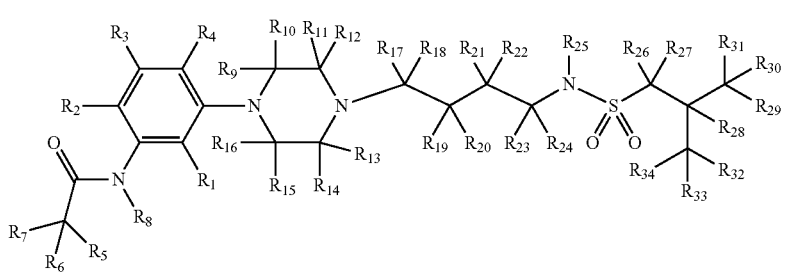

1 wherein:

$R_1$, $R_2$, $R_3$, and $R_4$ are independently selected from D, H or F;

$R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$ and $R_{24}$ are independently selected from D or H;

$R_{25}$ is selected from H, D or $CD_3$;

$R_{26}$, $R_{27}$, $R_{28}$, $R_{29}$, $R_{30}$, $R_{31}$, $R_{32}$, $R_{33}$, $R_{34}$ are independently selected from D and H;

$R_{29}$ and $R_{32}$ are joined together to form cyclic rings including cyclohexyl, cycloheptyl, cyclopentyl, cyclobutyl or cyclopropyl.

Deuterium (D or $^2H$) is a stable non-radioactive isotope of hydrogen (H) and has an atomic weight of 2.0144. Hydrogen occurs naturally as a mixture of the isotopes $^1H$, D ($^2H$), and T ($^3H$ or tritium). The natural abundance of deuterium is 0-015%. One of ordinary skill in the art recognizes that in all compounds containing H atom, H actually represents a mixture of H and D, with about 0-015% of D. The compounds with a level of D that have been enriched to be greater than its natural abundance of 0.015%, should be considered unnatural and as a result novel as compared to their corresponding non-enriched counterparts.

The carbon-hydrogen bonds contain a naturally occurring distribution of hydrogen isotopes, namely $^1H$ or protium (about 99.9844%), $^2H$ or deuterium (D) (about 0.0156%), and $^3H$ or tritium (in the range between about 0.5 and 67 tritium atoms per $10^{18}$ protium atoms). Higher levels of deuterium incorporation produce a detectable Kinetic Isotope Effect (Werstiuk, N. H.; Dhanoa, D. S.; Timmins, G. Can J. Chem. 1979, 57, 2885; Werstiuk, N. H.; Dhanoa, D. S.; Timmins, G. Can J. Chem. 1983, 61, 2403), that could have an effect on the pharmacokinetic, pharmacologic and/or toxicologic properties of deuterium containing compounds in comparison to compounds having naturally occurring levels of deuterium and their corresponding hydrogen (protium) analogs. The present invention disclosed herein describes novel compounds of formula I containing higher content of deuterium (>1%), synthesis and uses thereof for the treatment of anxiety disorders including, General Anxiety Disorder (GAD), Panic Disorder (PD), Post-Traumatic Stress Disorder (PTSD), Social Phobia (SP), Health Anxiety (Hypochondriasis), depression, major depressive disorders, unipolar depression, bipolar I depression disorder, bipolar II depression disorder, treatment-resistant depression, single episodic and recurrent major depressive disorders, depression in the medically ill, attention deficit hyperactivity disorder (ADHD), attention deficit disorder (ADD), Obsessive-Compulsive Disorder (OCD), Obsessive-Compulsive Personality Disorder (OCPD), Autism Spectrum Disorder (ASD), schizophrenia, psychosis, epilepsy, seizures, hot flashes due to menopause, age-related macular degeneration (AMD), premature ejaculation, male erectile dysfunction, sexual dysfunction, obesity, eating disorders, bulimia nervosa, anorexia nervosa, angina, migraine, pain, nociception, sleep disorders, insomnia, fibromyalgia, alcohol withdrawal, autism, Rett's syndrome, cyclothymic disorder, neural injury, neurodegenerative diseases, Parkinson's disease, Parkinson's disease psychosis, Huntington disease, Alzheimer's disease, frontotemporal dementia, cognitive impairment associated with age-related dementia, Alzheimer's disease, schizophrenia, psychosis, depression, pain or discomfort associated with surgery and pain or discomfort associated with medical illness.

shown in a chemical structure of a compound, a small amount of protium may still be present. Higher levels of deuterium content in a compound can be produced either by Hydrogen-Deuterium (H-D) exchange or by synthesizing the compound for specific deuteration. The H-D exchange is readily achieved in case of H atoms attached to heteroatoms for example in cases of carboxylic acids ($CO_2H$), amides, $CONHR$, sulfonamides ($SO_2NH_2$), alcohols (OH), basic amines ($NH_2$), etc. However, these incorporated D attached to hetero atoms (O, N, S) etc, readily revert back to H upon exposure to water or any acidic compounds containing H atoms. The preferred deuterium containing compounds are the ones which contain D directly attached to carbon atoms of the structure of the compounds of this invention.

In some embodiments, the deuterium enrichment in the compounds of the present invention is greater than about 4%, 5%, 6%, 7%, 8%, 9% or 10%. In other embodiments, the deuterium enrichment in the compounds of the present invention is greater than about 20%. In further embodiments, the deuterium enrichment in the compounds of the present invention is greater than about 50%. In some embodiments, the deuterium enrichment in the compounds of the present invention is greater than about 70%. In some embodiments, the deuterium enrichment in the compounds of the present invention is greater than about 90%.

This invention is concerned with deuterium-enriched compounds of structural formula 1, derivatives thereof and pharmaceutically acceptable salts and compositions thereof,

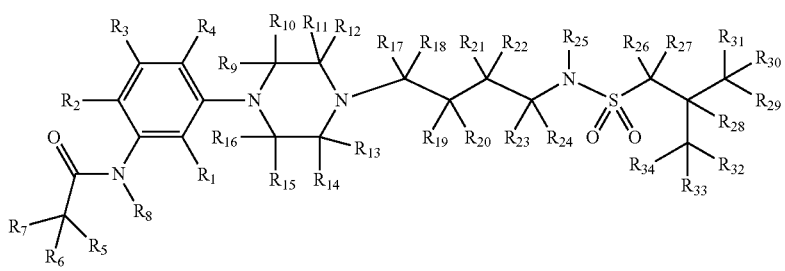

Suitable modifications of certain carbon-hydrogen bonds into carbon-deuterium bonds may generate novel substituted compounds of formula 1 with unexpected and non-obvious improvements of pharmacological, pharmacokinetic and toxicological properties in comparison to their hydrogen analogs. This invention relies on the judicious and successful application of chemical kinetics to drug design. Deuterium incorporation levels in the compounds of the invention are significantly higher than the naturally-occurring levels and are sufficient to induce at least one substantial improvement as described herein. All percentages given for the amount of D present are mole percentages.

Deuterium enrichment refers to the percentage of incorporation of deuterium at a given site on the compound instead of a hydrogen atom. For example, deuterium enrichment of about 1% means that in about 1% of molecules in a given compound a particular site is occupied by deuterium. Because the naturally occurring distribution of deuterium is about 0.0156%, deuterium enrichment in compounds synthesized using non-enriched starting materials is about 0.0156%.

It can be a significant synthetic challenge to produce 100% deuterium at a specific site of a compound. When 100% deuteration is recited or a deuterium atom is specifically wherein:
$R_1$, $R_2$, $R_3$, and $R_4$ are independently selected from D, H, F;
$R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$ and $R_{24}$ are independently selected from D and H;
$R_{25}$ is selected from H, D, $CD_3$;
$R_{26}$, $R_{27}$, $R_{28}$, $R_{29}$, $R_{30}$, $R_{31}$, $R_{32}$, $R_{33}$, $R_{34}$ are independently selected from D and H;
$R_{29}$ and $R_{32}$ are joined together to form cyclic rings including cyclohexyl, cycloheptyl, cyclopentyl, cyclobutyl and cyclopropyl;
wherein D is Deuterium atom present in the compounds of formula 1 and about 1%-100% enrichment of deuterium is incorporated.

In another embodiment, the present invention provides a novel, deuterium enriched compound of formula 1 or a pharmaceutically acceptable salt thereof, wherein at least one or all of the H atoms are substituted with D (deuterium atom) and the abundance of deuterium incorporated in the compounds is at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 365, 37%, 38%, 39%, 40%, 41%, 42%, 43%, 44%, 45%, 46%, 47%, 48%, 49%, 50%, 51%, 52%, 53%, 545, 55%, 56%, 57%, 58%, 59%, 60%, 61%, 62%, 63%, 64%, 65%, 66%, 67%, 68%, 69%, 70%, 71%, 72%, 73%, 74%, 755, 76%, 77%, 78%, 79%, 80%, 81%, 81%, 83%, 84%, 85%, 86%, 87%, 88%, 89%, 90%, 91%, 92%, 93%, 94%, 95%, 96%, 97%, 98%, 99% and 100%.

The present invention provides an amount of a novel deuterium-compound of formula 1.

Examples of amounts include, but are not limited to (a) at least about 0.01, 0.02, 0.03, 0.04, 0.05, 0.1, 0.2, 0.3, 0.4, 0.5, to 1 mole, (b) at least about 0.1 mole, and (c) at least about 1 mole of the compound I. The present amounts also cover lab-scale (e.g., gram scale), kilo-lab scale, and industrial or commercial scale (e.g., multi-kilogram or larger scale) quantities as these will be more useful in the actual manufacture of a pharmaceutical, industrial/commercial scale refers to the amount of product that would be produced in a batch that was designed for clinical testing, formulation, sale/distribution to the public, etc.

In another embodiment, the present invention provides a novel, deuterium enriched compound of formula 1 or pharmaceutically acceptable salt thereof.

In another embodiment, the present invention provides a novel, deuterium enriched compound of formula 1 or a pharmaceutically acceptable salt thereof, wherein abundance of deuterium at each carbon center is at least about 5%, 10%, 15%, 20%, 25%, 30%, 40%, 50%, 60% 70%, 80%, 90% and 100%.

One advantage of the compounds of the invention is that they were discovered to be both 5-HT modulators e.g. agonists, inverse agonists or antagonists and have SSRI type effects. These compounds are effective in treating, preventing or curing 5-HT related disorders or diseases In one aspect, the compounds of the invention are 5-HT modulators (agonists, partial agonists, antagonists or inverse agonists) and/or selective serotonin reuptake inhibitors (SSRI). The compounds of the present invention are $5\text{-HT}_{1A}$ receptor modulators specifically $5\text{-HT}_{1A}$ partial agonists as shown by their high binding affinity (Ki) in the range of 1 nM-1000 nM and functional activity ($EC_{50}$) in the range of 1 nM-2000 nM for the $5\text{-HT}_{1A}$ receptor. These compounds also show activity for other 5-HT receptor subtypes as well as dopamine receptors in the range of 10 nM-2500 nM. The compounds of this invention also show activity as selective serotonin reuptake inhibitors in the range of 1 nM-1000 nM.

In another embodiment, the present invention provides a novel method for the treatment of age-related macular degeneration (AMD), epilepsy, seizures, premature ejaculation, sexual dysfunction, male erectile dysfunction, obesity, eating disorders, anorexia, bulimia, sleep disorders, insomnia, angina, migraine, pain, sleep disorder, insomnia, fibromyalgia, alcohol withdrawal, autism, Rett's syndrome, attention deficit hyperactivity disorder (ADHD), attention deficit disorder (ADD), general anxiety disorders, major depressive disorders, unipolar depression, bipolar I depression disorder, bipolar II depression disorder, cyclothymic disorder, treatment-resistant depression, single episodic and recurrent major depressive disorders, depression in the medically ill, neurodegenerative diseases, Parkinson's disease, Huntington disease, Alzheimer's disease, frontotemporal dementia, cognitive impairment associated with age-related dementia, schizophrenia, and psychosis, Parkinson's disease, Huntington disease, stroke, post-traumatic syndrome, surgery, comprising, administering to a patient in need thereof a therapeutically effective amount of a deuterium-enriched compound of the formula 1, or a pharmaceutically acceptable salt thereof.

In another embodiment, the present invention provides the use of an amount of deuterium-enriched compound of the present invention for the manufacture of a medicament, e.g., for the treatment of age-related macular degeneration (AMD), epilepsy, seizures, premature ejaculation, sexual dysfunction, male erectile dysfunction, obesity, eating disorders, anorexia, bulimia, sleep disorders, insomnia, angina, migraine, pain, sleep disorder, autism, Rett's syndrome, attention deficit hyperactivity disorder (ADHD), attention deficit disorder (ADD), general anxiety disorders, major depressive disorders, unipolar depression, bipolar I depression disorder, bipolar II depression disorder, cyclothymic disorder, treatment-resistant depression, single episodic and recurrent major depressive disorders, depression in the medically ill, neurodegenerative diseases, Parkinson's disease, Huntington disease, Alzheimer's disease, frontotemporal dementia, cognitive impairment associated with age-related dementia, schizophrenia, Parkinson's disease, Huntington disease, stroke, post-traumatic syndrome, other medical illnesses.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

Definitions

The compounds of the present invention may have various isomers including all stereoisomers, tautomeric or rotamers, all isomers and solvates are considered to be part of the present invention. All processes used to prepare compounds of the present invention and intermediates made therein are considered to be part of the present invention.

"Therapeutically effective amount" includes an amount of a compound of the present invention that is effective when administered alone or in combination with other medicaments to treat the desired condition or disorder. "Therapeutically effective amount" includes an amount of the combination of compounds claimed that is effective to treat the desired condition or disorder. The combination of compounds is preferably a synergistic combination.

"Pharmaceutically acceptable salts" refer to derivatives of the disclosed compounds wherein the parent compound is modified by making acid or base salts thereof. Examples of the pharmaceutically acceptable salts include, but not limited to, mineral or organic acid salts of the basic residues. The pharmaceutically acceptable salts include but not limited to HCl, DCl, HBr, DBr, HI, DI, acetic, trifluoroacetic, citric, ascorbic, benzoin, methanesulfonic, benzenesulfonic, bicarbonic, carbonic, ethane disulfonic, edetic, fumaric, maleic, lactic, malic, mandelic, gluconic, glutamic, glycolic, glycollyarsanilic, lauryl, hexylresorcinic, hyrdabamic, hydroxymaleic, hydroxynaphthoic, isethionic, lactobionic, napsylic, nitric, oxalic, pamoic, pantothenic, phenyllacetic, phosphoric, polygalacturonic, propionic, salicyclic, stearic, subacetic, succinic, sulfamic, sulfanilic, sulfuric, tannic, tartaric, toluenesulfonic, and p-bromobenzenesulfonic.

Treating or treatment includes any effect, e.g. lessening, reducing, modulating, or eliminating, that results in the improvement of the disease or disorder or condition.

Routes or methods of administering drug includes topical, oral, subcutaneous, and via injection into the body or a specific site.

Combination therapy (use of compounds of this invention in combination with other compounds or medicaments) or co-therapy includes the administration of compounds of the present invention (deuterium-enriched compounds of formula 1) and at least a second agent as part of a specific treatment regimen intended to provide the beneficial effect from the co-action of these therapeutic agents. The beneficial effect of the combination includes, but is not limited to pharmacokinetic or pharmacodynamic co-action resulting from the combination of therapeutic agents. Administration of these therapeutic agents in combination typically is carried out over a defined time period (usually weeks, days, hours, or minutes depending upon the combination selected). "Combination therapy" may, but generally is not, intended to encompass the administration of two or more of these therapeutic agents as part of separate monotherapy The preparation of deuterated sulfonamide compounds of formula 1 are illustrated in schemes 1-6 below and in the examples given in Table 1. The schemes and examples are given for the purpose of illustrating the invention and not for limiting the scope or spirit of the invention.

PREPARATION OF DEUTERATED ISOBUTYLSULFONAMIDE 10

Preparation of 3-N-Acetyl($d_3$)-Aniline 2

1,3-Diaminobenzene 1 is converted to 2 by selective monoacetylation with deuterated acetyl chloride ($CD_3COCl$) or deuterated acetic anhydride as illustrated in scheme 1 below. To a solution of 1 (5 g) in dicholoromethane or acetonitrile is added acetyl chloride-$d_3$ (1 equiv) at 0° C. and the mixture stirred for 1 hour. The reaction mixture is poured onto ice water and extracted with methylene chloride and washed with saturated aqueous solution of sodium bicarbonate. The organic phase is dried over anhydrous sodium sulfate, filtered, concentrated in vacuo and the product isolated by purification by flash chromatography to give 2 (4.5 g).

Preparation of Deuterated 3-N-Acetyl($d_3$)-Aniline (2,4,6 $d_3$) 3

To a mixture of 2 (1 g) and deuterated water $D_2O$ (2 ml) is added concentrated hydrochloric acid (HCl) (1 ml) and the reaction mixture is heated in microwave at 180° C. for 30 min. The mixture is allowed to attain room temperature and diluted with dichloromethane (100 ml). The mixture is cooled to 0° C. and saturated aqueous solution of sodium bicarbonate is added slowly to neutralize the reaction mixture. The organic phase is washed with saturated solution of sodium chloride (brine) and the organic phase is dried over sodium sulfate and filtered. The filterate is concentrated in vacuo to yield 3 (0.85 g). Mass spectral analysis: m/e 157 (M+1).

Preparation of 3-N-Acetyl($d_3$)-aminophenyl($d_3$)-piperazine 5

To a mixture of 3 (0.85 g) and potassium carbonate (3 equiv) in 1-butanol is added deuterated or undeuterated bis (2-chloroethyl)amine 4 (1 equiv) and the mixture refluxed for 24 hours. The mixture is allowed to cool down to room temperature and diluted with dichloromethane. The mixture is made alkaline by adding aqueous solution of NaOH. The mixture is then extracted with more dichloromethane, dried over anhydrous sodium sulfate, filtered, and the filtrate concentrated in vacuo. The product isolated by flash chromatography to give 5 (0.9 g).

Preparation of 3-N-Acetyl($d_3$)-aminophenyl($d_3$)-4-N-Boc-(aminobutyl)piperazine 7

A mixture of 5 (0.9 g), triethylamine (1.5 equiv) and N-Boc-butyl tosylate 6 (1.1 equiv) in acetonitrile is stirred for 24 hours. The mixture is diluted with dichloromethane and ice-water and stirred. The mixture is further treated with saturated aqueous solution of sodium hydroxide, stirred and the organic phase separated. The organic phase is dried over anhydrous sodium sulfate, filtered and the filtrate is concentrated in vacuo to give 7 (0.1.25 g) after flash chromatography.

Preparation of 3-N-Acetyl($d_3$)-aminophenyl($d_3$)-4-N-Boc-(aminobutyl)piperazine 8

To a solution of 7 (1.25 g) in dichloromethane at 0° C. is added trifluoroacetic acid (3 equiv) and the reaction mixture stirred for one and a half hour. The volatiles are removed in vacuo and the resulting precipitate is washed with diethyl ether and the precipitate is dried to yield 8 (0.85 g). Mass spectral analusis (m/e): 297 (M+1).

The N-Boc protection group is also removed by treatment of 7 with Hydrochloric acid in dioxane (HCl, dioxane).

Preparation of deuterated N-[3-{4-(4-(2-Methyl($d_3$)-propan($d_7$)-1-sulfonylamino)-butyl)-piperazin-1-yl}-phenyl($d_3$)]acetamide($d_3$) 10

To a solution of the amine 8 (0.45 g) in dichloromethane at 0° C. is added deuterated isobutyl($d_9$)-sulfonyl chloride 9 (1 equiv) and the reaction mixture stirred for 4 hours. The mixture is concentrated by removing volatiles in vacuo, then diluted with dichloromethane and washed with aqueous sodium bicarbonate solution and then water. The organic phase is dried over sodium sulfate, then filtered and the filtrate concentrated. The resulting residue is flash chromatographed to give the target product 10 (0.50 g). Mass spectral analysis: (m/e) 426 (M+1).

Preparation of deuterated N-[3-{4-(4-(cyclohexyl-methanesulfonylamino-butyl)-piperazin-1-yl]-phenyl ($d_3$)]-acetamide($d_3$) 12

To a solution of the amine 8 (0.4 g) in dichloromethane at 0° C. is added deuterated cyclohexylmethyl ($d_{10}$)-sulfonyl chloride 11 (1 equiv) and the reaction mixture stirred for 4 hours. The mixture is concentrated in vacuo, then diluted with dichloromethane and washed with aqueous sodium bicarbonate solution and then water. The organic phase is dried over sodium sulfate, then filtered and the filtrate concentrated. The resulting residue is flash chromatographed to give the target product 12 (0.54 g). Mass spectral analysis: (m/e) 470 (M+1).

SCHEME 1.
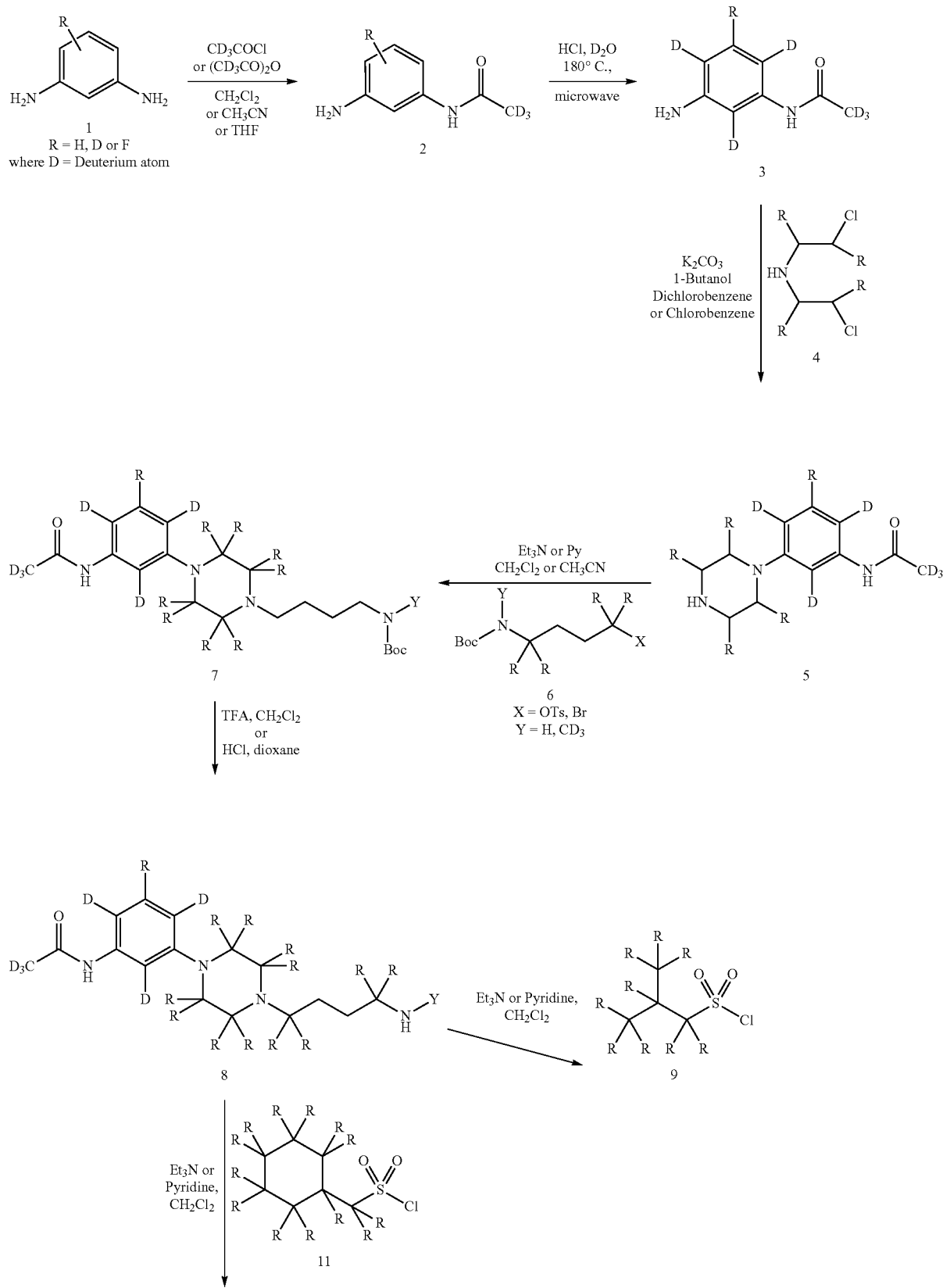

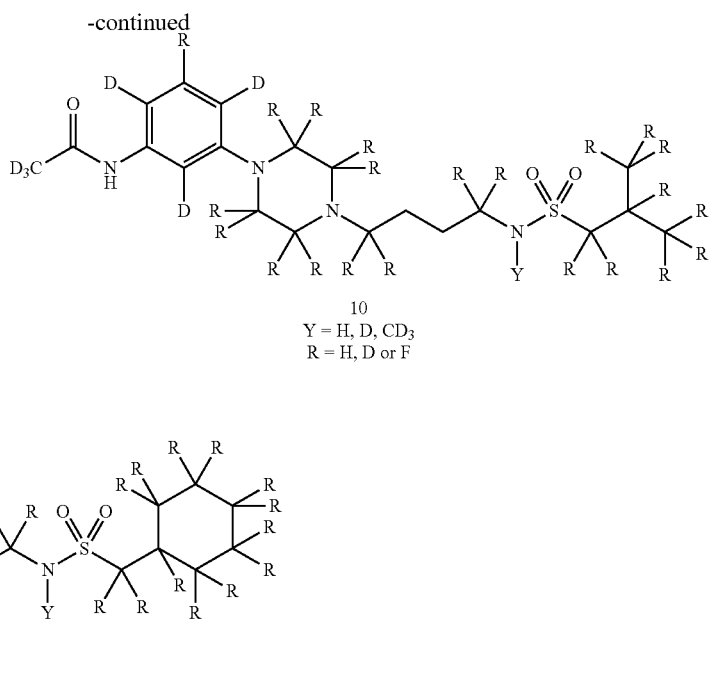

10
Y = H, D, CD₃
R = H, D or F

12
Y = H, D, CD₃
R = H, D or F

Preparation of isobutyl sulfonamide 10 and cyclohexylmethyl sulfonamide 12 from an alternative starting material 3-nitroanile is illustrated in scheme 2 and described below.

Preparation of Deuterated 3-Nitro-aniline-(d₃) 14

Deuterated 3-Nitro-aniline (2,4,6-d₃) 14 (1.2 g) is prepared from 3-nitroaniline 13 (1.5 g) by heating with D₂O and conc. HCl in microwave at 180° C. for 30 min as shown in scheme 2. Mass spectral analysis: m/e 142 (M+1). The method is described above for the preparation of 3 in scheme 1.

Preparation of Deuterated 3-Nitrophenyl(d₃)-piperazine 15

3-Nitro-aniline (d₃) 14 (1.2 g) is converted to 3-nitrophenyl (d3)-piperazine 15 (1.3 g) by refluxing in butanol with potassium carbonate and bis(chloroethyl)amine 4 for 36 hours as described for the preparation of 5. Mas spectral analysis: m/e 211 (M+1).

Preparation of 3-Nitrophenyl(d₃)amino-4-N-Boc-(aminobutyl)piperazine 16

15 (1.3 g) was converted to 16 (1.7 g) by alkylating with 6 (1 equiv) in dichloromethane and triethylamine as described above for the preparation of 7. Mass spectal analysis: m/e 382 (M+1).

Preparation of 3-Nitrophenyl(d₃)-4-piperazinyl-butylamine 17

The amine 17 (1.2 g) is prepared from the corresponding N-Boc derivative 16 (1.7 g) by TFA in dichloromethane as described above in the preparation of 8. Mass spectral analysis: m/e 282 (M+1).

Preparation of deuterated 3-Nitrophenyl(d₃)-piperazinyl-4-n-butyl-isobutylsulfonamide 18

The amine 17 (0.6 g) is converted to the sulfonamide 18 (0.65 g) by treating with isobutylsulfonyl chloride 9 in dichloromethane and triethylamine as described above for the preparation of the sulfonamide 10. Mass spectral analysis: m/e 411 (M+1).

Preparation of deuterated 3-Nitrophenyl(d₃)-piperazinyl-4-n-butyl-cyclohexylmethylsulfonamide 19

Similarly the amine 17 (0.5 g) is converted to the deuterated cyclohexylmethyl sulfonamide 19 (0.6 g) as described for the preparation of the sulfonamide 12.

Preparation of deuterated 3-Aminophenyl(d₃)-piperazinyl-4-n-butyl-isobutylsulfonamide 20

A solution of 18 (0.6 g) in methanol (30 ml) was added to a mixture of tin chloride (2.2 g) and conc. HCl (6 ml) in methanol (30 ml) at −10° C. and the mixture is stirred while allowing to attain room temperature slowly. The reaction mixture is stirred for additional 24 hours at room temperature and then quenched with aqueous sodium bicarbonate solution. The mixture is extracted with dichloromethane, dried over sodium sulfate and filtered. The filtrate is concentrated in vacuo and purified by flash column chromatography to give 20 (0.45 g). Mass spectral analysis: m/e 381 (M+1).

The 3-(nitrophenyl)piperazinyl-n-butyl-isobutylsulfonamide 18 is also transformed to the amine 20 by catalytic hydrogenation of 18 using Pd/C as catalyst.

Preparation of deuterated 3-Aminophenyl(d₃)-piperazinyl-4-n-butyl-cyclohexylsulfonamide 21

Deuterated 3-Nitrophenyl(d₃)-piperazinyl-4-n-butyl-cyclohexylmethylsulfonamide 19 (0.5 g) is converted to the corresponding amine 21 in a similar manner as described above for the preparation of the isobutyl analog 20. Reduction of 19 with tin chloride and conc. HCl gave 21 (0.35 g). Mass spectral analysis: m/e 425 (M+1).
SCHEME 2.
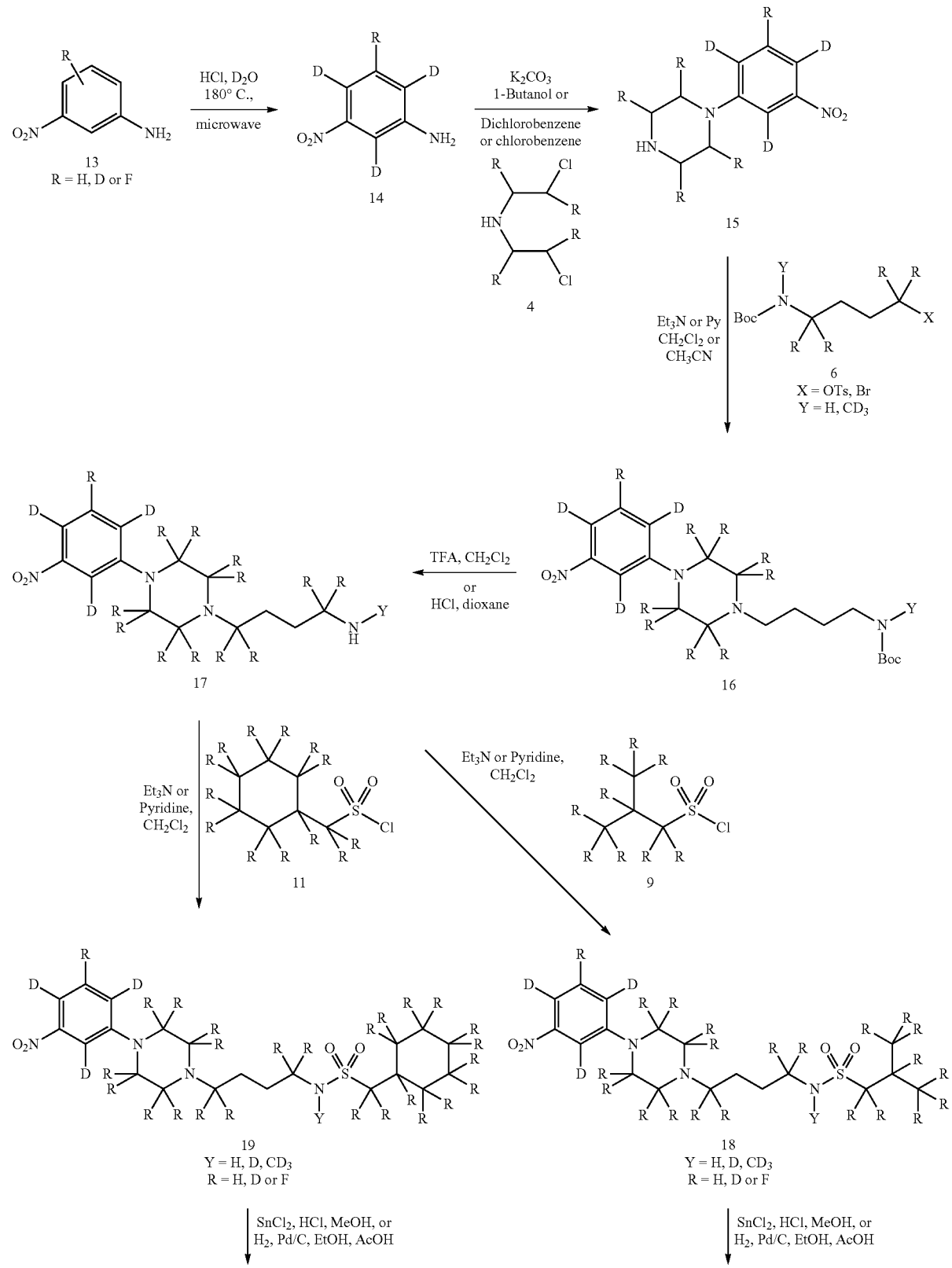

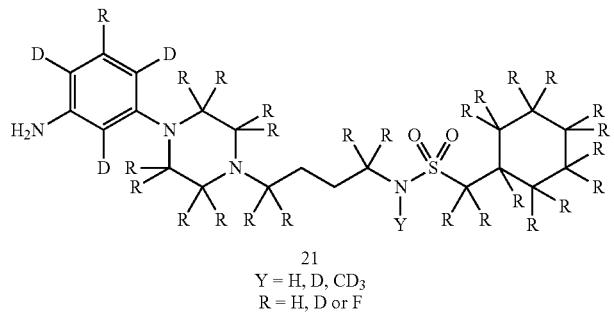

21
Y = H, D, CD₃
R = H, D or F

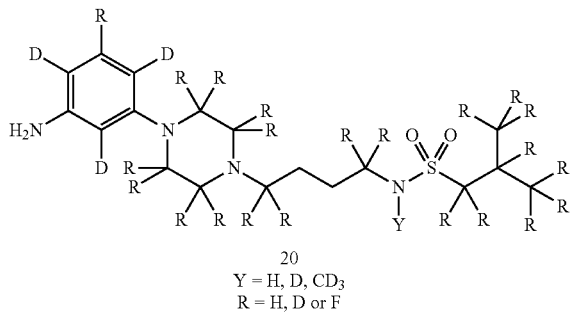

20
Y = H, D, CD₃
R = H, D or F

The acetylation of substituted sulfonamide anilines 20 and 21 with deuterated acetyl chloride (d₃) are illustrated in scheme 3.

Preparation of 3-(Acetylaminophenyl)piperazinyl-4-butyl)-isobutyl-sulfonamide 10

To a solution of deuterated amine 20 (0.4 g) in dichloromethane (4 ml) at 0° C. is added pyridine (1 ml), and deuterated acetyl(d₃) chloride (1 equiv) and the reaction mixture allowed to warm to room temperature and then stirred overnight. The reaction mixture is concentrated to a residue in vacuo. Dichloromethane (50 ml) is added to the residue and washed with aqueous solution of sodium bicarbonate, then brine and water. The organic phase is dried over sodium sulfate, filtered and the filtrate is concentrated in vacuo. The resulting material is purified by flash column chromatography to give the target compound, isobutyl sulfonamide, 10 (0.42 g). Mass spectral analysis: m/e 426 (M+1).

Preparation of 3-(Acetylaminophenyl)piperazinyl-4-butyl)-cyclohexylmethyl-sulfonamide 12

To a solution of deuterated amine 21 (0.3 g) in dichloromethane (4 ml) at 0° C. is added pyridine (1 ml), and deuterated acetyl(d₃) chloride (1 equiv) and the reaction mixture allowed to warm to room temperature and then stirred overnight. The reaction mixture is concentrated to a residue in vacuo. Dichloromethane (50 ml) is added to the residue and washed with aqueous solution of sodium bicarbonate, then brine and water. The organic phase is dried over sodium sulfate, filtered and the filtrate is concentrated in vacuo. The resulting material is purified by flash column chromatography to give the target compound, cyclohexylmethyl sulfonamide, 12 (0.26 g). Mass spectral analysis: m/e 470 (M+1).

The preparation of pharmaceutically acceptable salts such as deuterated-hydrochloric acid (DCl) salt is illustrated in scheme 4.

Preparation of 3-(Acetylaminophenyl)piperazinyl-4-butyl)-isobutyl-sulfonamide 10.DCl Deuterated methanol (CD₃OD) is added in excess to the sulfonamide 10 (0.28 g) and the solution stirred for 10 min under N₂ followed by addition of D₂O and HCl in ether. The volatile are removed in vacuo to give the deuterochloride (DCl) salt of 10.DCl (0.32) in which the acidic protons on the sulfonamide and amide are also exchanged for D.

Preparation of 3-(Acetylaminophenyl)piperazinyl-4-butyl)-cyclohexylmethyll-sulfonamide 12. DCl Deuterated methanol (CD₃OD) is added in excess to the sulfonamide 12 (0.25 g) and the solution stirred for 10 min under N₂ followed by addition of D₂O and HCl in ether. The volatile are removed in vacuo to give the deuterochloride (DCl) salt of 12.DCl (0.28 g) in which the acidic protons on the sulfonamide and amide are also exchanged for D.

SCHEME 3.

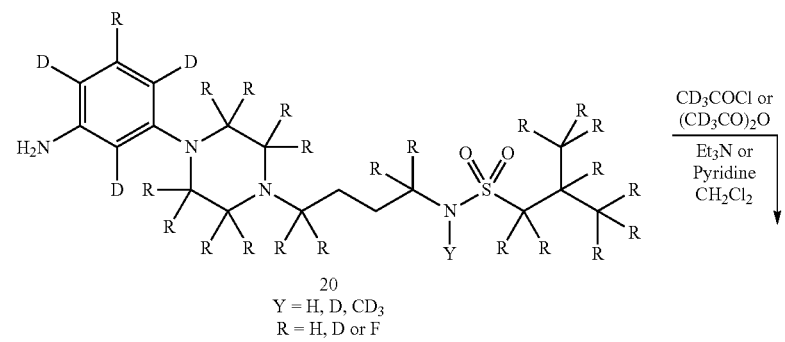

20
Y = H, D, CD₃
R = H, D or F

-continued
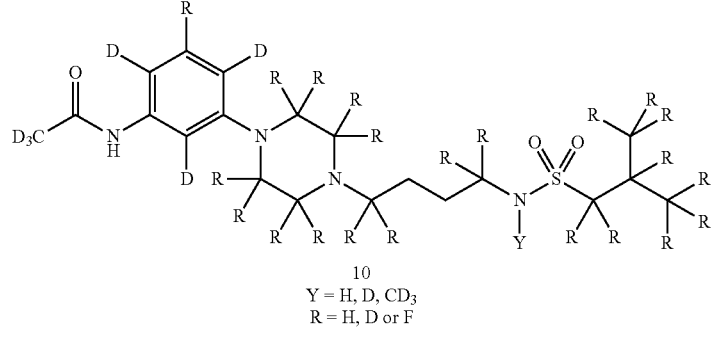
10
Y = H, D, CD$_3$
R = H, D or F
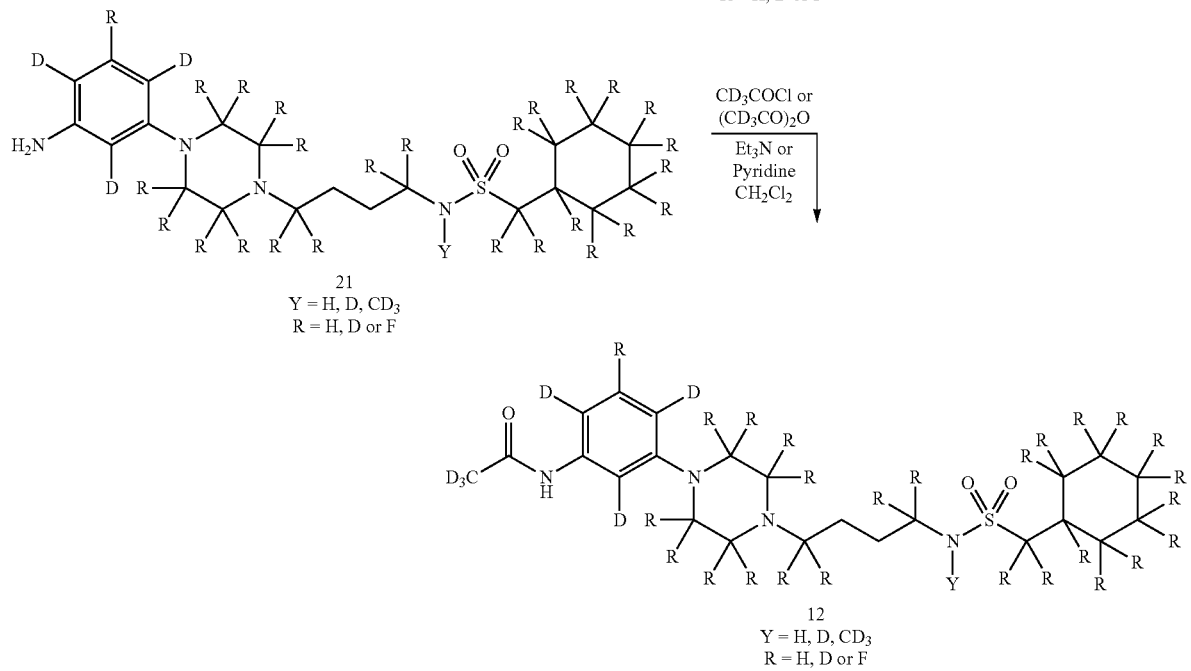
SCHEME 4.
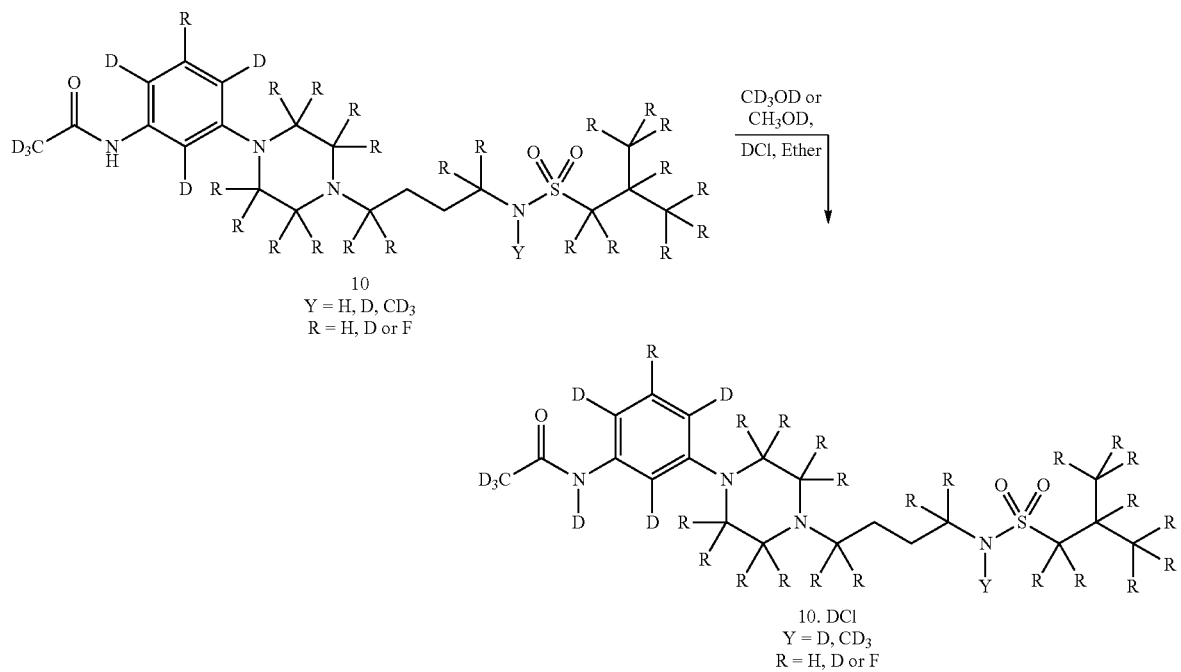

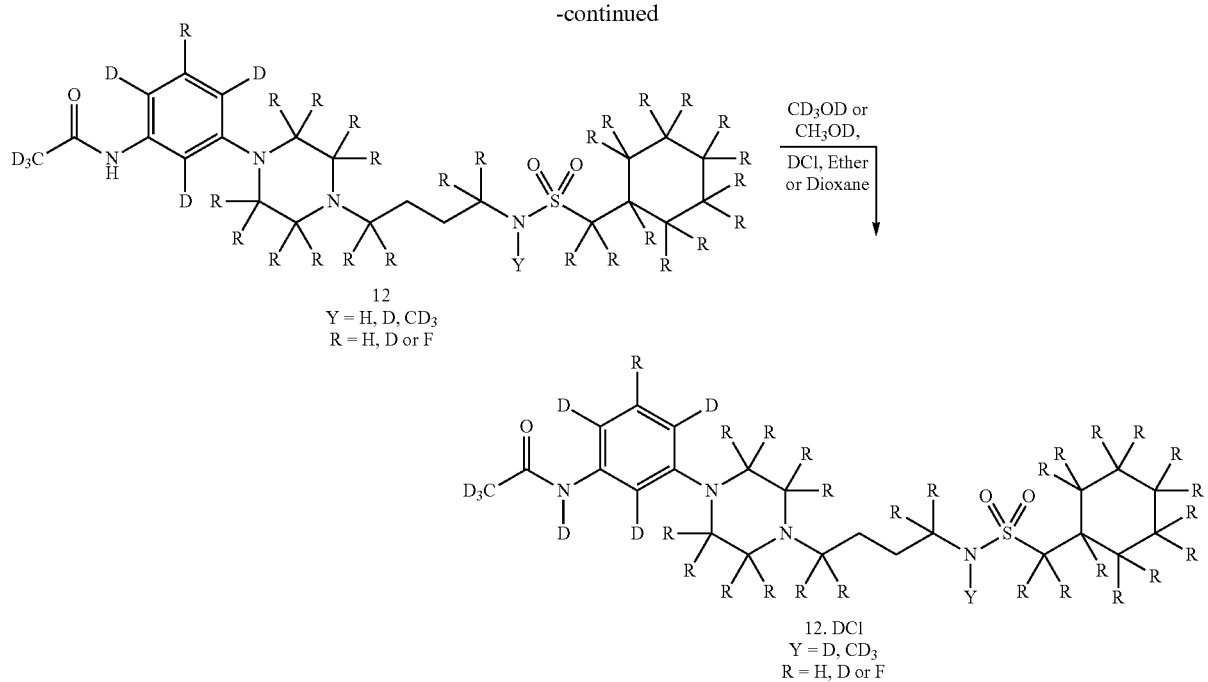

12
Y = H, D, CD$_3$
R = H, D or F

12. DCl
Y = D, CD$_3$
R = H, D or F

Preparation of Deuterated Isobutyl Sulfonyl Chloride 9

The deuterated isobutylsulfonyl chloride 9 is synthesized from the deuterated isobutyl alcohol (2-methylpropan-1-ol) as illustrated in Scheme 5 and described below.

To a stirred mixture of isobutyl alcohol-d$_9$ (2-methylpropan-1-ol-d$_9$) (5 g) and CBr$_4$ (1 equiv) in dichloromethane at 0° C. is added Ph$_3$P (1 equiv) under N$_2$. The mixture is stirred for one hour and allowed to warm to room temperature with stirring for additional one hour. The reaction mixture is cooled to 0° C. and quenched with methanol. The reaction mixture is concentrated and the residue is purified by flash chromatography to yield deuterated isobutyl bromide 23 (6.2 g).

The bromide 23 (3 g) is treated with aqueous solution of sodium sulfite (3 equiv) in water for 24 hours. The reaction mixture is filtered to isolate the precipitated product 24 (2 g) which is used in the next step in which 24 it treated with thinly chloride (2 equiv) in toluene for overnite. The excess unconsumed thionyl chloride is evaporated in vacuo and the residue is diluted with ice water and extracted with ether (3×50 mL). The ether phase is washed with aqueous sodium hydrogen sulfite and then water. The ether solution is dried over calcium chloride for 30 min. The removal of calcium chloride and solvent yields deuterated isobutylsulfonyl chloride 9 (1.6 g), as an oil. Mass spectral analysis: m/e 166 (M+1).

In another method to prepare 9, the bromide 23 (5.5 g) is treated with sodium sulfide (1.1 equiv) in N,N-dimethyl formamide for 12 hours. The mixture is quenched with ice and extracted with diethyl ether. The ethereal solution is washed with 5% HCl, 10% NaHCO$_3$, brine and dried over anhydrous MgSO$_4$, filtered and concentrated in vacuo to give the deuterated isobutyl mercaptan 25 (3 g).

To the deuterated isobutyl mercaptan 25 (3 g) is added acetic acid (10 mL) and ice (3.3 g) in a 100 ml round bottom flask which is then placed in an ice bath. Chlorine gas is passed through the solution for 30 min. The reaction temperature is kept at 0° C. The reaction mixture is stirred for an additional 30 min after the Cl$_2$ addition is ceased. The reaction mixture is diluted with ice-water (30 mL) and extracted with ether. The ether extracts are combined and then washed with saturated aqueous solution of sodium hydrogen sulfite, and water. The ether solution is dried over calcium chloride for 30 min, then filtered and the filtrate is concentrated to remove the solvent to give the deuterated isobutylsulfonyl chloride 9 (4.2 g).

SCHEME 5.

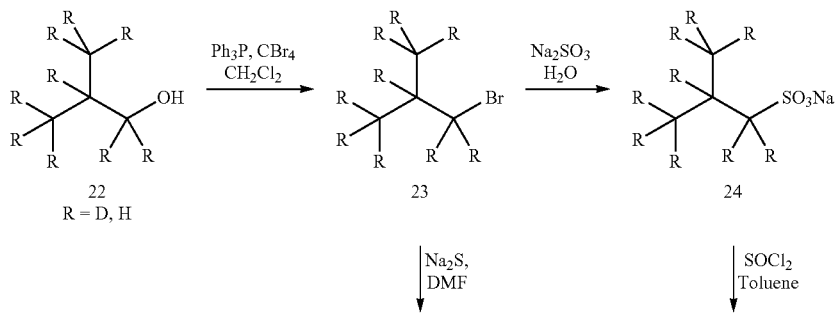

22
R = D, H

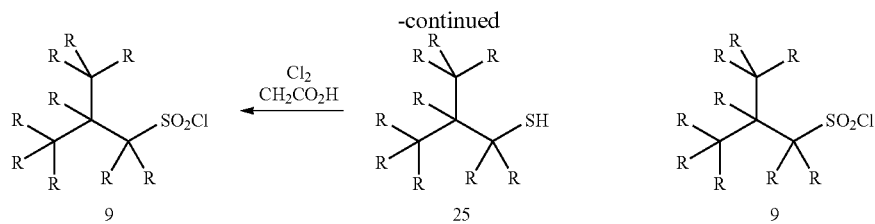

The deuterated cyclohexylmethyl sulfonyl chloride 11 is prepared as illustrated in scheme 6 below from the corresponding deuterated cyclohexylmethyl alcohol 26 using the methods as described above for the preparation of deuterated isobutylsulfonyl chloride 9 in scheme 5.

SCHEME 6.

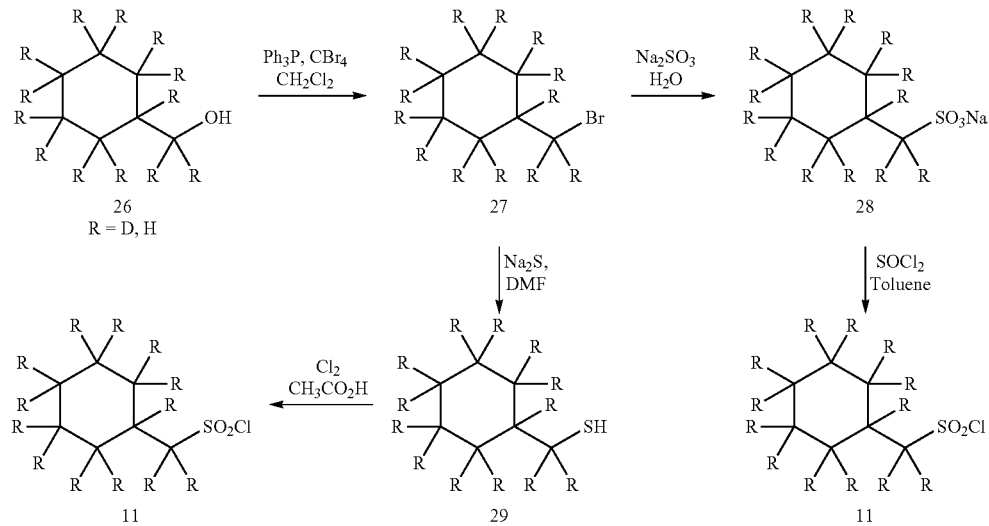

The compounds shown below in the Table 1 are prepared by using the methods described in the general procedures and schemes illustrated above and modifications thereof. Given below are compounds that are representative examples of the present invention.

TABLE 1

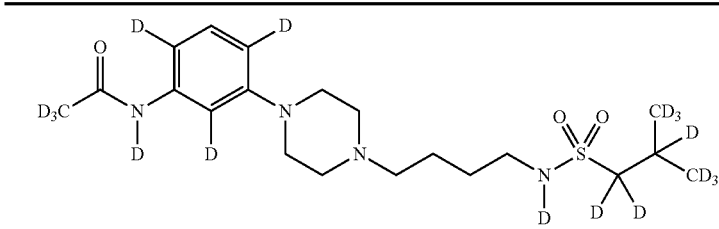

1

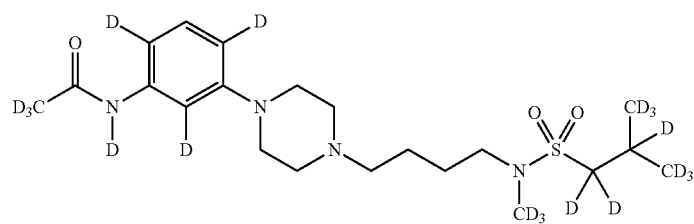

2

TABLE 1-continued
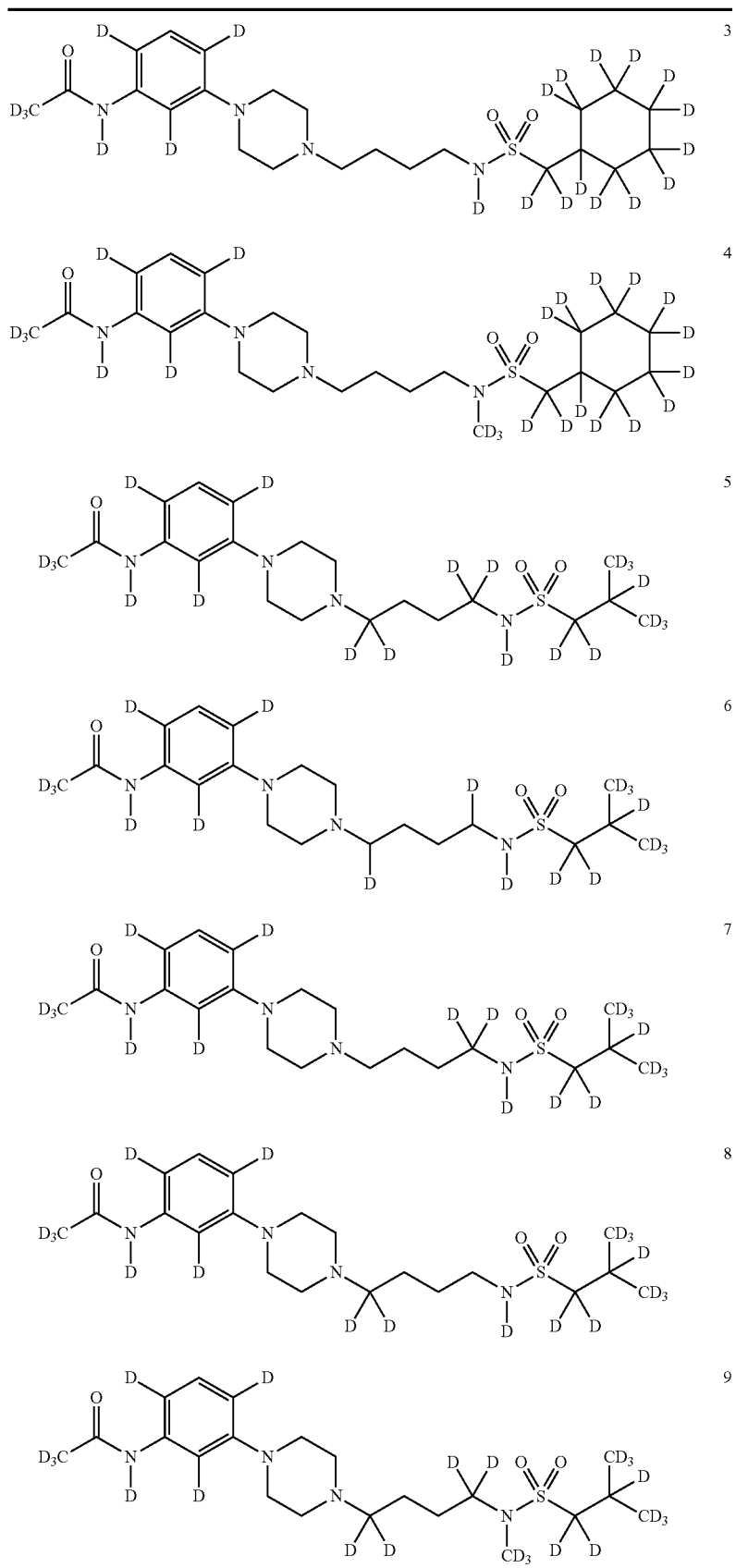

TABLE 1-continued
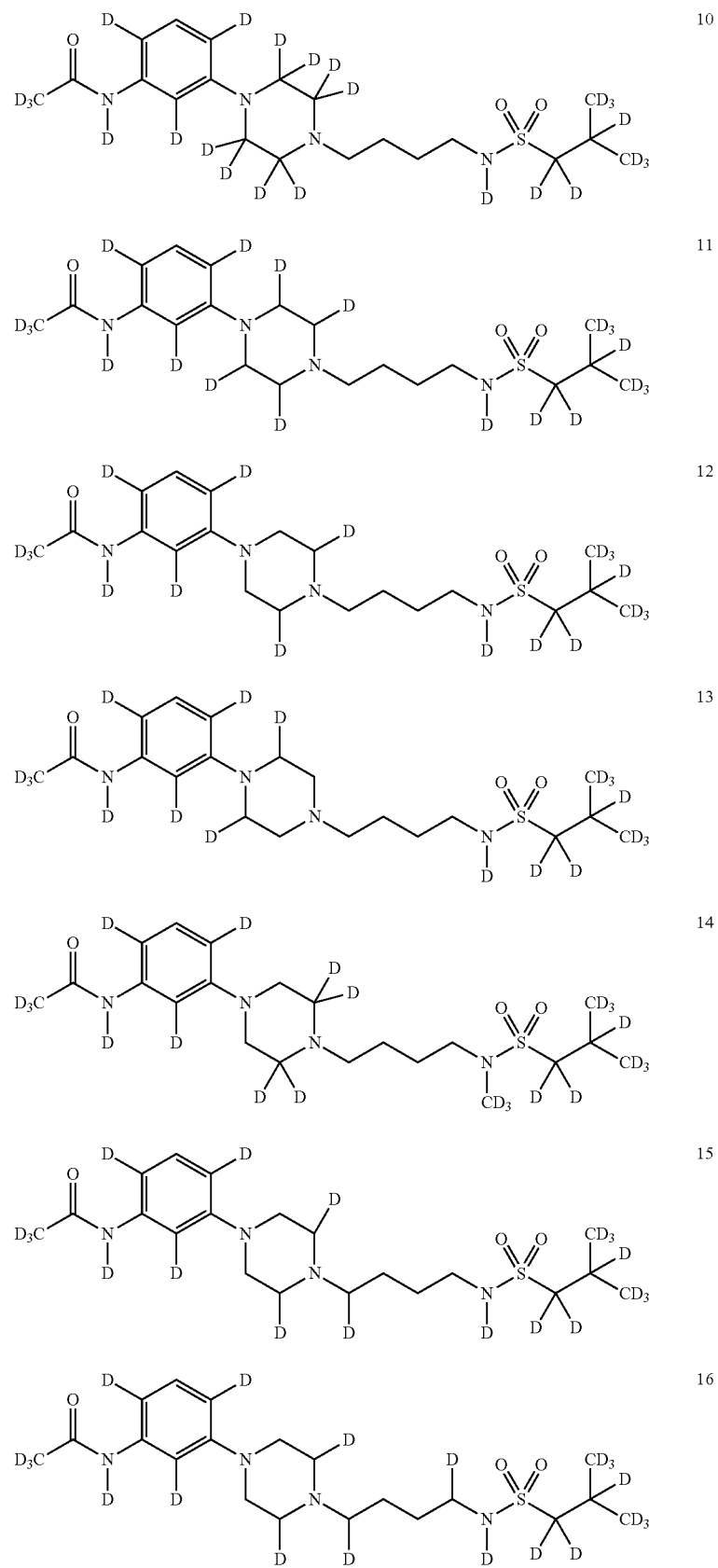

TABLE 1-continued
| | |
|---|---|
| 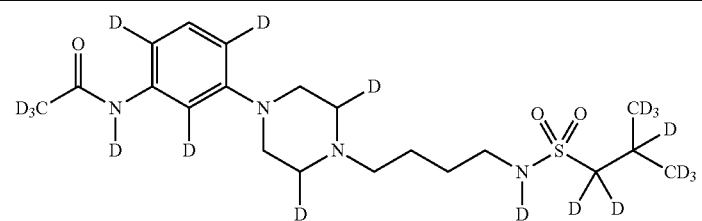 | 17 |
| 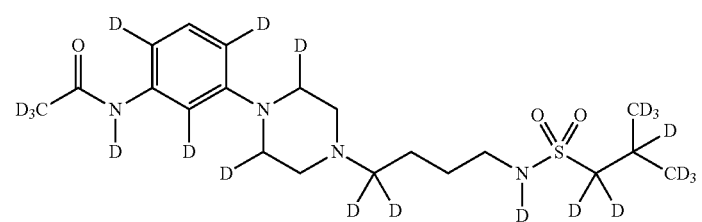 | 18 |
| 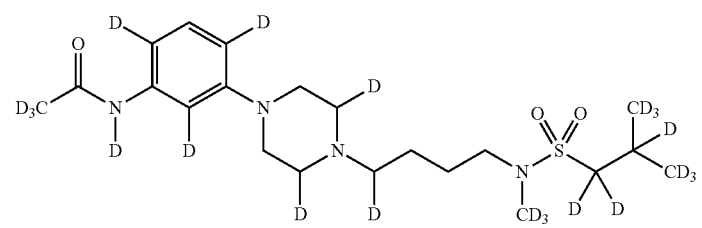 | 19 |
| 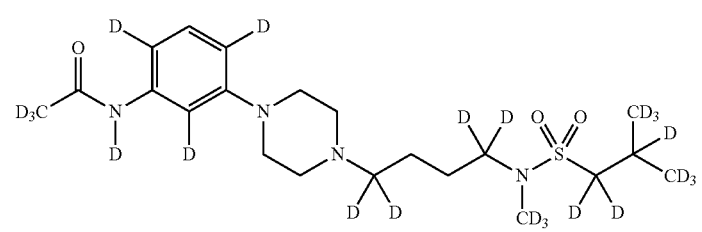 | 20 |
| 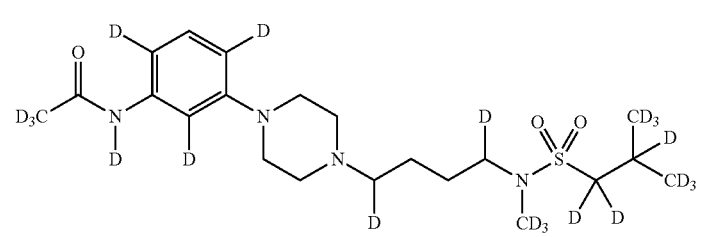 | 21 |
| 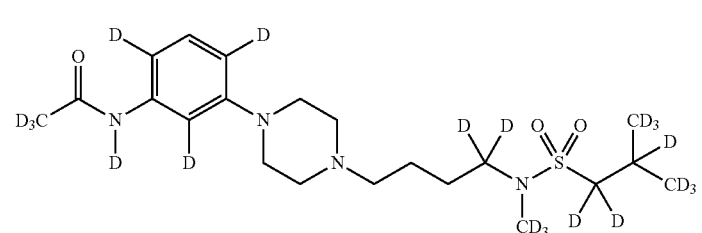 | 22 |
| 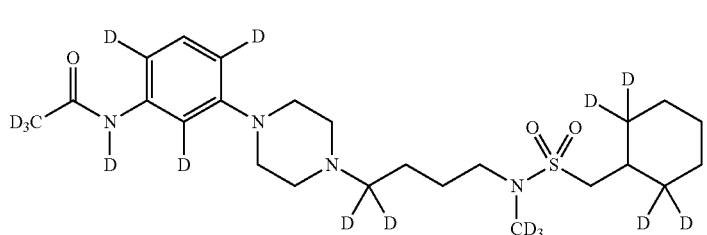 | 23 |

TABLE 1-continued
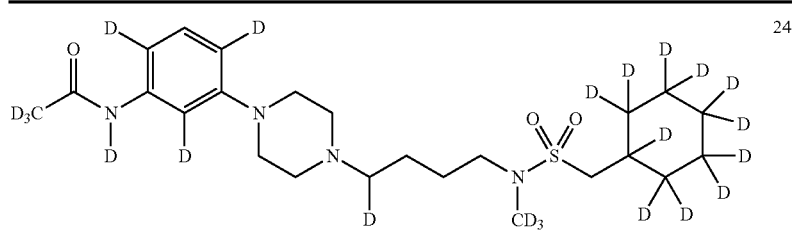 24
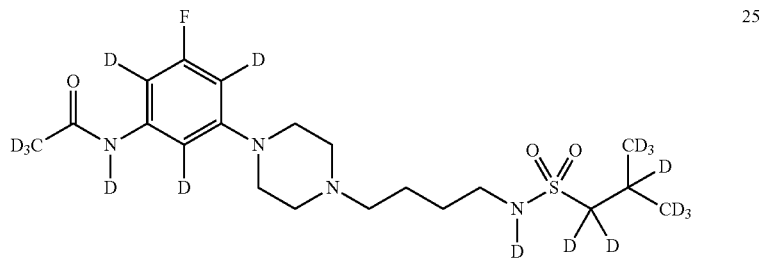 25
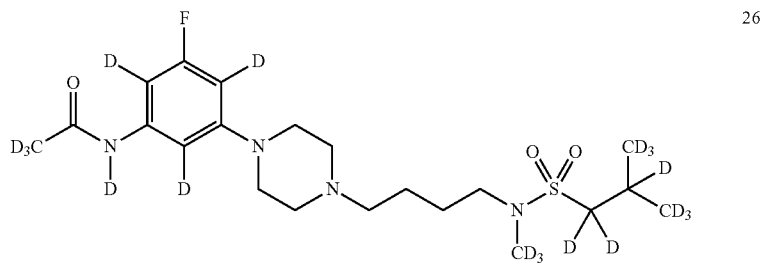 26
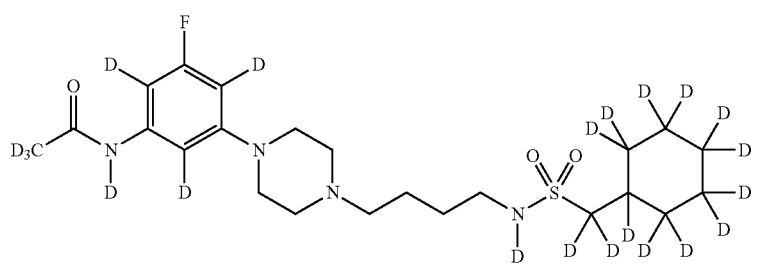 27
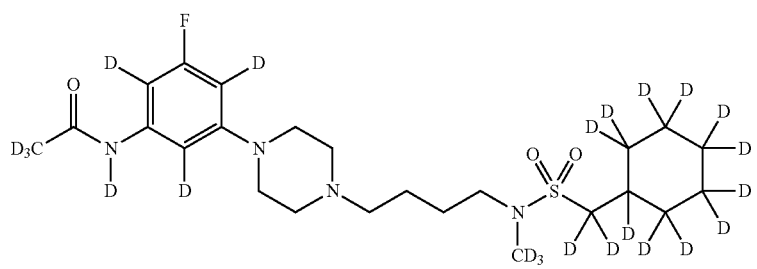 28
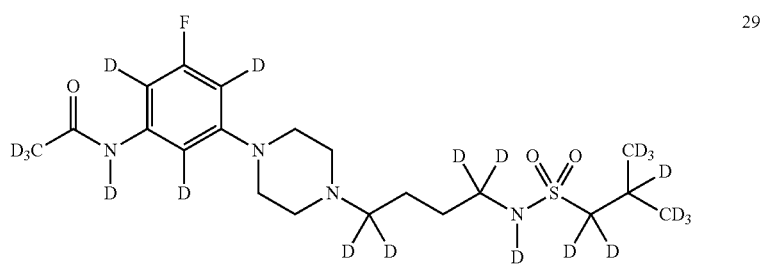 29

TABLE 1-continued
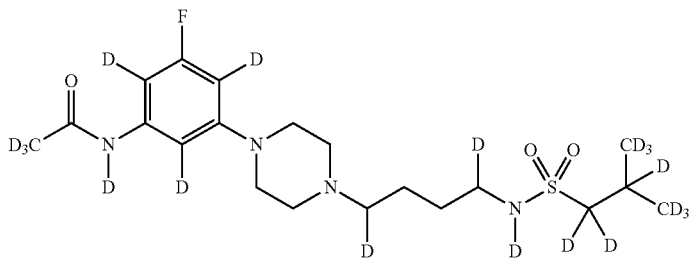
30
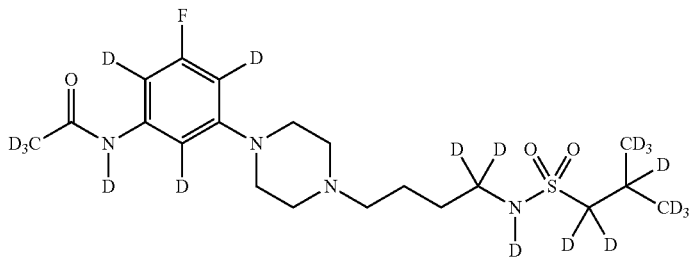
31
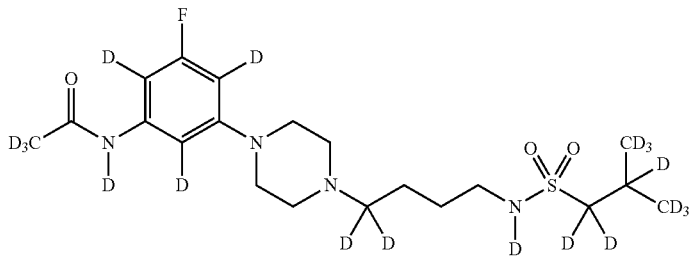
32
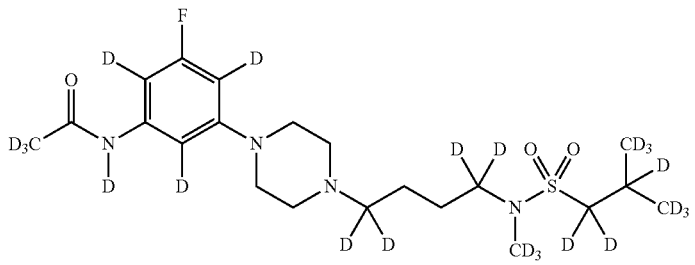
33
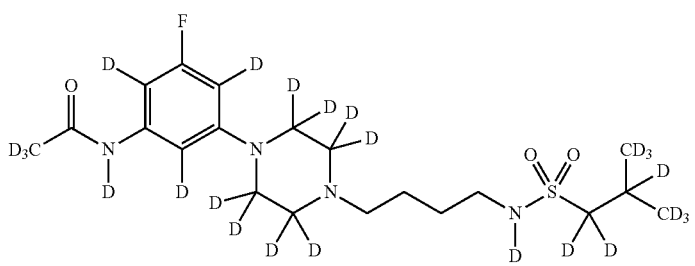
34
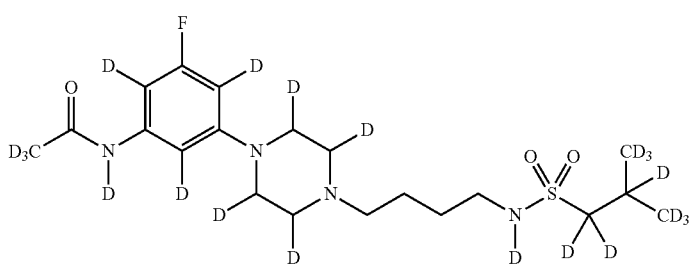
35

TABLE 1-continued
| | |
|---|---|
| 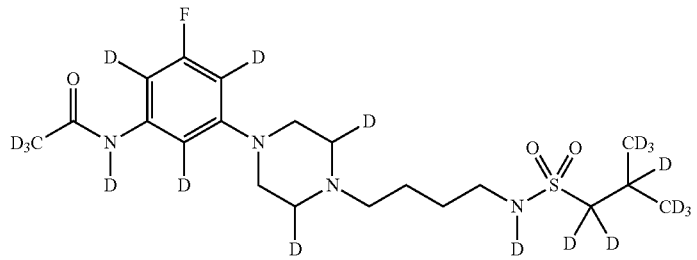 | 36 |
| 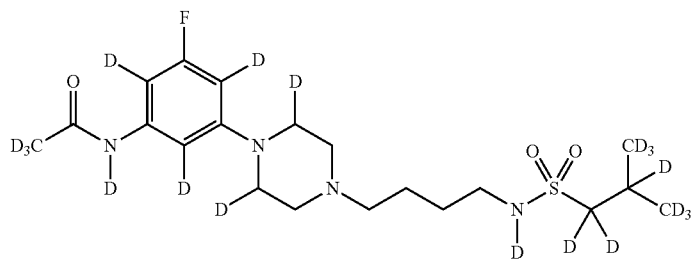 | 37 |
| 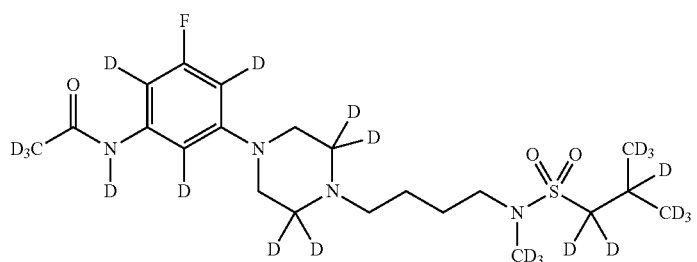 | 38 |
| 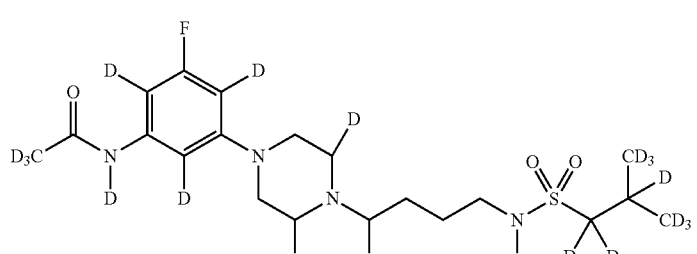 | 39 |
| 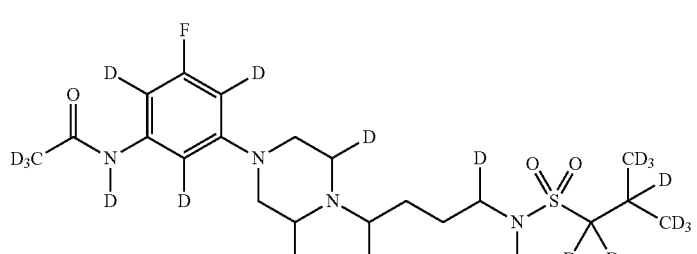 | 40 |
| 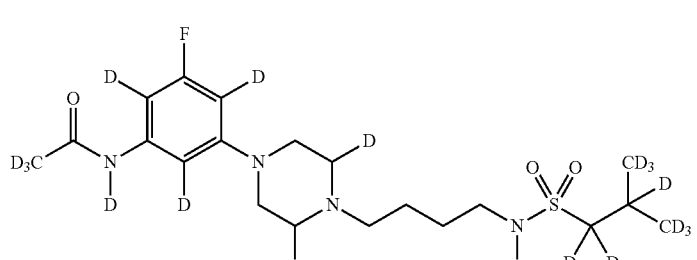 | 41 |

TABLE 1-continued
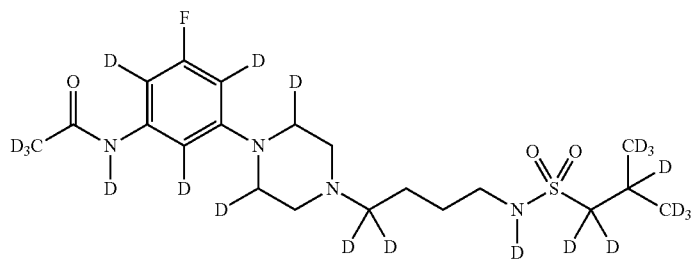
42
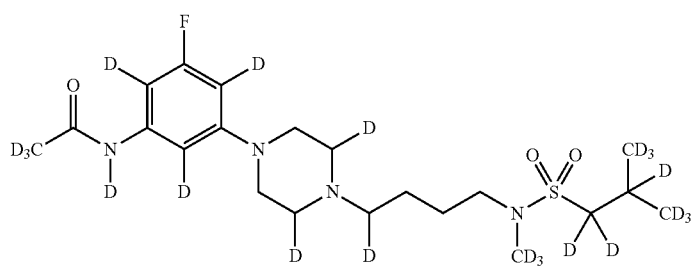
43
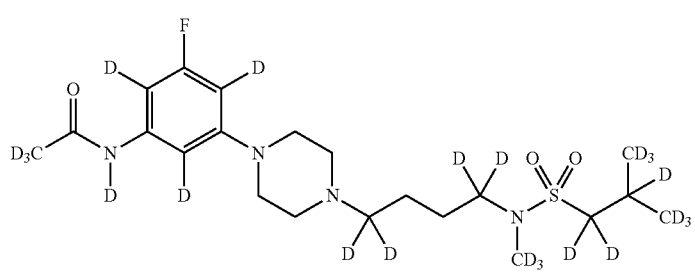
44
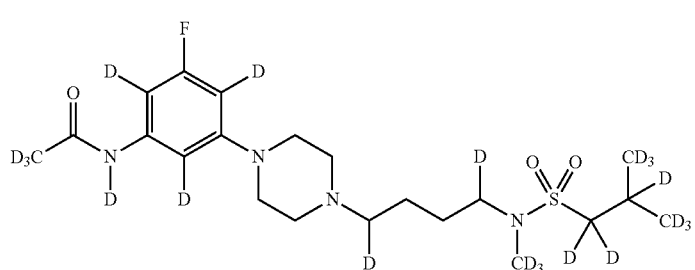
45
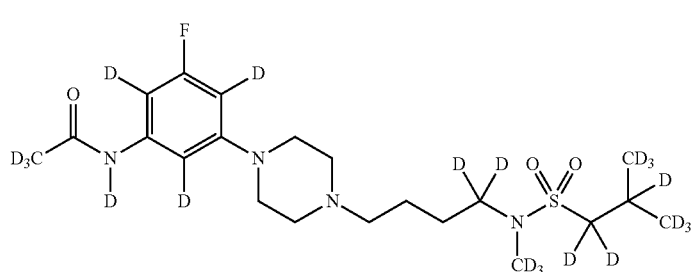
46
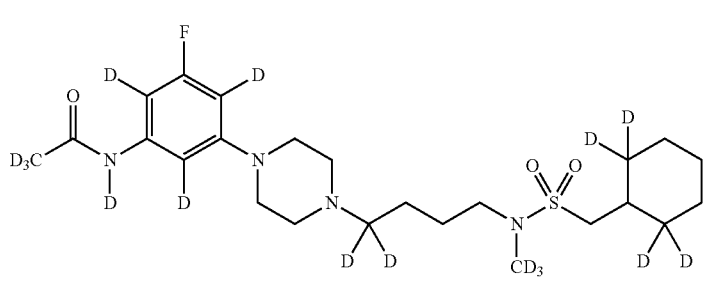
47

TABLE 1-continued

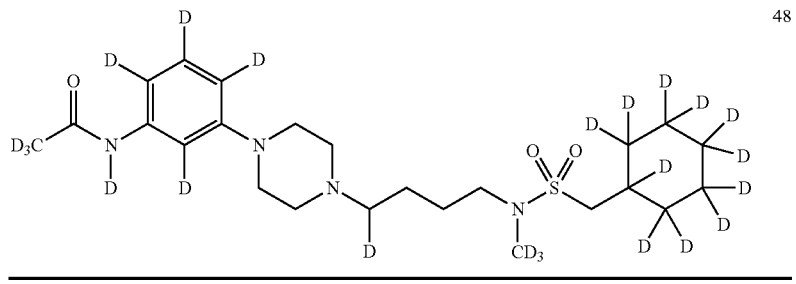

48

Equivalents

Those skilled in the art will recognize, or be able to ascertain using no more than routine experimentation, numerous equivalents to the specific procedures described herein. Such equivalents are considered to be within the scope of the invention and are covered by the following claims. Various substitutions, alterations, and modifications may be made to the invention without departing from the spirit and scope of the invention as defined by the claims. Other aspects, advantages and modifications are within the scope of the invention. The contents of all references, issued patents and published patent applications cited in this application are hereby incorporated by reference. The appropriate components, processes, and methods of those patents, applications and other documents may be selected for the invention and embodiments thereof.

What is claimed is:

1. A method of treating a disease or disorder selected from the group consisting of General Anxiety Disorder (GAD), Panic Disorder (PD), Post-Traumatic Stress Disorder (PTSD), Social Phobia (SP), Health Anxiety (Hypochondriasis), depression, major depressive disorder, unipolar depression, bipolar I depression disorder, bipolar II depression disorder, treatment-resistant depression, single episodic and recurrent major depressive disorders, depression in the medically ill, attention deficit hyperactivity disorder (ADHD), attention deficit disorder (ADD), Obsessive-Compulsive Disorder (OCD), Obsessive-Compulsive Personality Disorder (OCPD), Autism Spectrum Disorder (ASD), schizophrenia, psychosis, epilepsy, seizures, hot flashes due to menopause, age-related macular degeneration (AMD), premature ejaculation, male erectile dysfunction, sexual dysfunction, obesity, bulimia nervosa, anorexia nervosa, smoking cessation, angina, migraine, pain, nociception, insomnia, fibromyalgia, alcohol withdrawal, autism, Rett's syndrome, cyclothymic disorder, neural injury, Parkinson's disease, Parkinson's disease psychosis, Huntington disease, Alzheimer's disease, frontotemporal dementia, cognitive impairment associated with age-related dementia, pain or discomfort associated with surgery and pain or discomfort associated with medical illness, by administering a pharmaceutically effective dose of a deuterium-enriched compound of formula 1, or a pharmaceutically acceptable salt thereof,

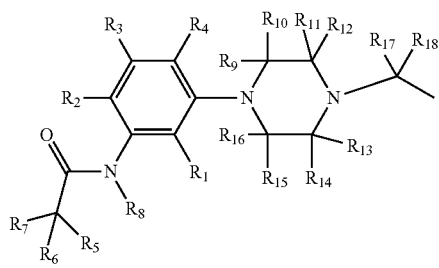

1

-continued

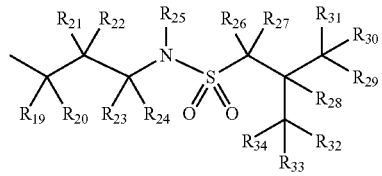

wherein:

$R_1$, $R_2$, $R_3$, and $R_4$ are independently selected from D, H and F;

$R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$ and $R_{24}$ are independently selected from D and H;

$R_{25}$ is selected from H, D and $CD_3$;

$R_{26}$, $R_{27}$, $R_{28}$, $R_{29}$, $R_{30}$, $R_{31}$, $R_{32}$, $R_{33}$, $R_{34}$ are independently selected from D and H;

$R_{29}$ and $R_{32}$ are joined together to form cyclic rings including cyclohexyl, cycloheptyl, cyclopentyl, cyclobutyl and cyclopropyl;

the abundance of deuterium in compounds of formula 1 is at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 91%, 92%, 93%, 94%, 95%, 96%, 97%, 98%, 99% and 100%.

2. The method of claim 1, wherein a compound is selected from the group consisting of,

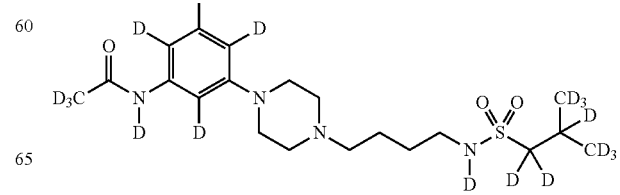

61
-continued
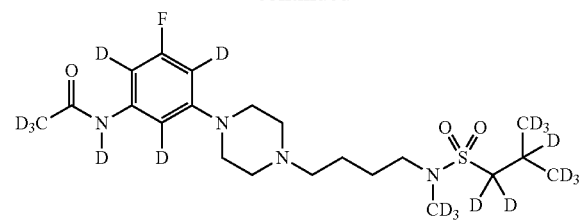
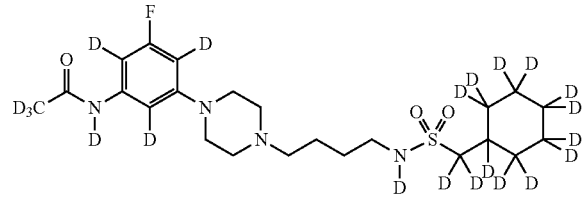
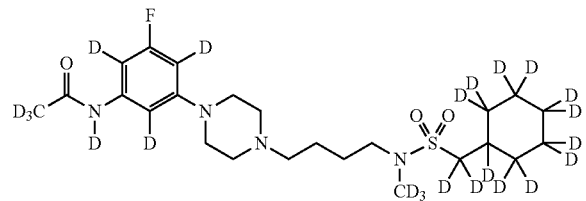
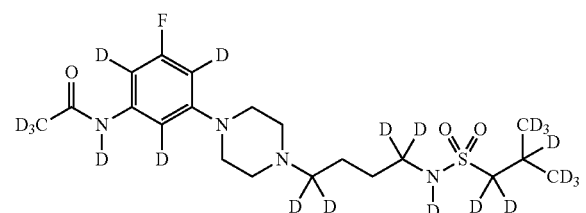
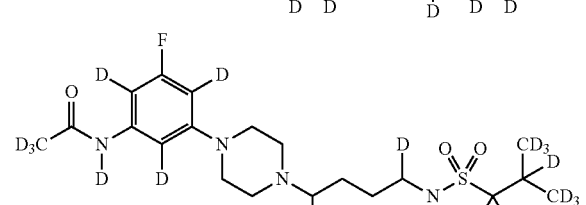
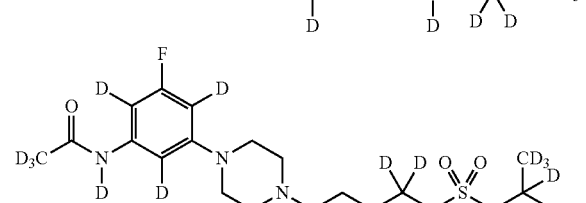
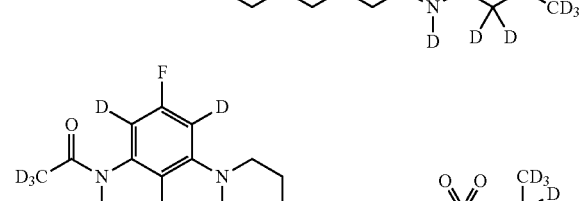
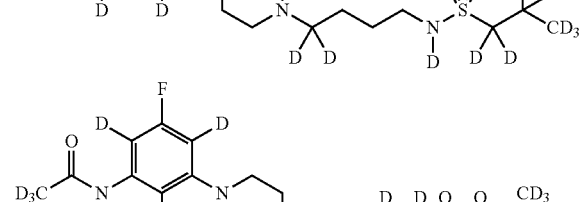
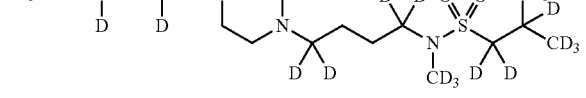
62
-continued
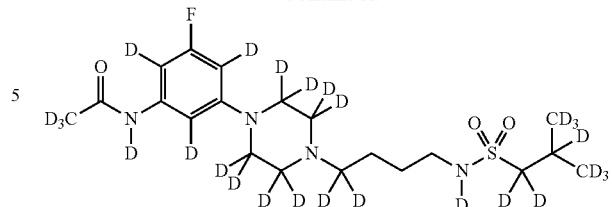
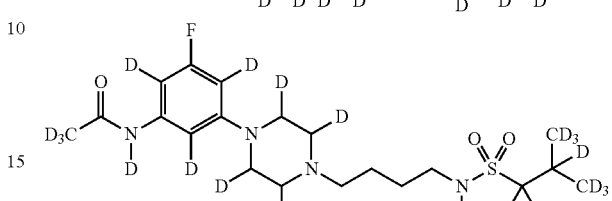
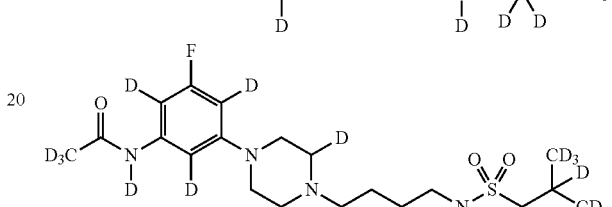
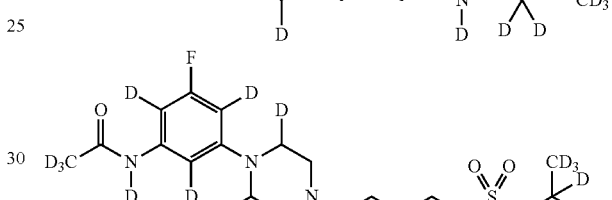
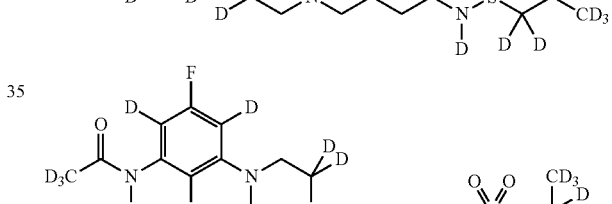
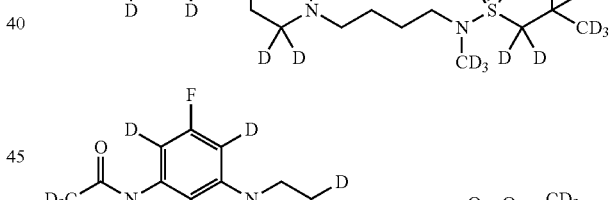
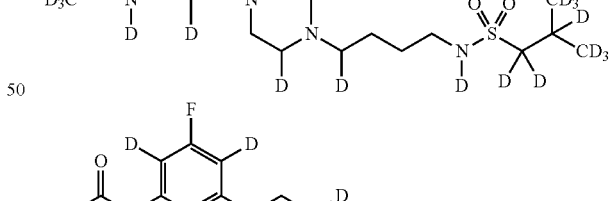
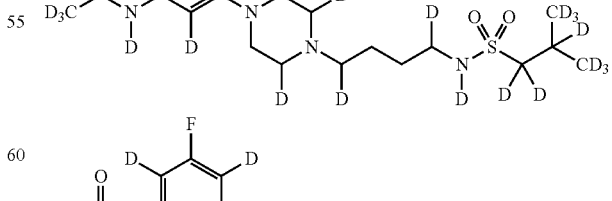
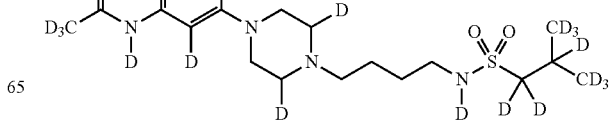

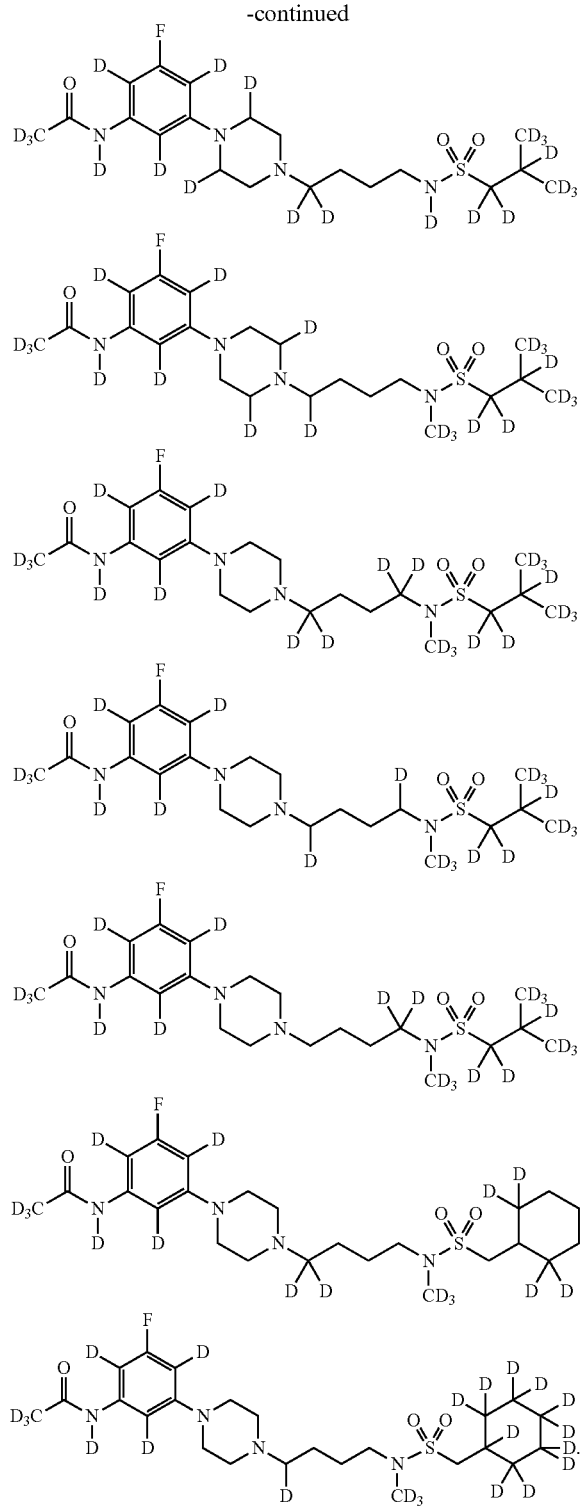

3. The method of claim 1 wherein the disease or disorder is selected from the group consisting of General Anxiety Disorder (GAD), Panic Disorder (PD), Post-Traumatic Stress Disorder (PTSD), Social Phobia (SP), Health Anxiety (Hypochondriasis), depression, major depressive disorder, unipolar depression, bipolar I depression disorder, bipolar II depression disorder, treatment-resistant depression, single episodic and recurrent major depressive disorders, depression in the medically ill, attention deficit hyperactivity disorder (ADHD), attention deficit disorder (ADD), epilepsy, partial epilepsy, temporal lobes epilepsy, seizures, hot flashes due to menopause, age-related macular degeneration (AMD), premature ejaculation, obesity, bulimia nervosa, anorexia nervosa, Parkinson's disease, Parkinson's disease psychosis, and smoking cessation.

4. The method of claim 3 wherein the disease or disorders are attention deficit hyperactivity disorder (ADHD) and attention deficit disorder.

5. The method of claim 4 wherein the treatment includes the administration of a drug selected from the group consisting of caffeine, amphetamine, dextroamphetamine, L-lysine-D-amphetamine and methylphenidate 6. The method of claim 3 wherein the disease is age-related macular degeneration (AMD).

7. The method of claim 6 wherein the treatment includes the administration of a vascular endothelial growth factor (VEGF) inhibitor selected from the group consisting of pegaptinib, vatalinib, and pazopanib.

8. The method of claim 6 wherein the treatment includes the administration a sphingosine 1-phosphate (S1P$_1$) agonist selected from the group consisting of fingolimod, ponesimod, and 2-amino-2-(5-(5-(3-chloro-4-propoxyphenyl)-1,2,4-oxadiazol-3-yl)benzofuran-2-yl)propane-1,3-diol.

9. The method of claim 3 wherein the disease treated is selected from the group consisting of epilepsy, partial epilepsy, temporal lobes epilepsy, and seizures.

10. The method of claim 9 wherein the treatment includes the administration of one or more drugs selected from the group consisting of phenytoin, sodium valproate, carbamazepine, phenobarbital, pregabalin, gabapentin, topamax, tiagabine, vigabetrin, oxcarbazepine, levitracetam, eslicarbazepine acetate, and lamotrigine.

11. The method of claim 3 wherein the disease or disorder is premature ejaculation.

12. The method of claim 11 wherein the treatment includes the administration of a selective serotonin reuptake inhibitors (SSRI) selected from the group consisting of dapoxetine, fluoxetine, paroxetine, sertraline, citalopram, (S)-citalopram and bupropion.

13. The method of claim 3 wherein the disease is Parkinson's disease and Parkinson's disease psychosis.

14. The method of claim 3 wherein the disease or disorder is selected from obesity, bulimia nervosa and anorexia nervosa.

15. The method of claim 14 wherein the treatment includes the administration of one or more drugs selected from 2-methyl-1-phenylpropan-2-amine, 2,3,4,5-bis-(gemdimethylmethylenedioxy)-β-D-fructopyranose sulfamate, naltrexone and bupropion.

16. The method of claim 13 wherein the treatment includes the administration of one or more drugs selected from the group consisting of pimavanserin, levodopa, carbidopa, pramipexol, ropinirole and bromocriptine.

17. The method of claim 3 wherein the disease or disorder is hot flashes due to menopause.

18. The method of claim 17 wherein the treatment includes the administration a selective serotonin reuptake inhibitors (SSRI) selected from the group consisting of dapoxetine, fluoxetine, paroxetine, sertraline, citalopram, (S)-citalopram and bupropion.

19. The method of claim 3 wherein the disease or disorder is General Anxiety Disorder (GAD), Panic Disorder (PD), Post-Traumatic Stress Disorder (PTSD), Social Phobia (SP), Health Anxiety (Hypochondriasis), depression, major depressive disorder, unipolar depression, bipolar I depression disorder, bipolar II depression disorder, treatment-resistant depression, single episodic and recurrent major depressive disorders, depression in the medically ill.

20. The method of claim 19 wherein the treatment includes the administration a drug selected from vilazodone, samidorphan, buprenorphine , aripiprazole, and selective serotonin reuptake inhibitors (SSRI) selected from the group consisting of dapoxetine, fluoxetine, paroxetine, sertraline, citalopram, (S)-citalopram and bupropion.

* * * * *